United States Patent
Wagner et al.

(10) Patent No.: US 10,160,834 B2
(45) Date of Patent: Dec. 25, 2018

(54) LOW VISCOSITY POLYORGANOSILOXANES COMPRISING QUATERNARY AMMONIUM GROUPS, METHODS FOR THE PRODUCTION AND THE USE THEREOF

(71) Applicant: Momentive Performance Materials GmbH, Leverkusen (DE)

(72) Inventors: Roland Wagner, Bonn (DE); Karl-Heinz Stachulla, Leverkusen (DE); Katharina Streicher, Leverkusen (DE); Christian Wenske, Solingen (DE)

(73) Assignee: Momentive Performance Materials Inc., Waterford, NY (US)

( * ) Notice: Subject to any disclaimer, the term of this patent is extended or adjusted under 35 U.S.C. 154(b) by 139 days.

(21) Appl. No.: 15/209,121

(22) Filed: Jul. 13, 2016

(65) Prior Publication Data

US 2018/0016397 A1    Jan. 18, 2018

(51) Int. Cl.

| | | |
|---|---|---|
| *C08G 77/14* | (2006.01) | |
| *C08G 77/04* | (2006.01) | |
| *A61K 8/06* | (2006.01) | |
| *A61K 8/891* | (2006.01) | |
| *A61Q 5/02* | (2006.01) | |
| *A61Q 5/06* | (2006.01) | |
| *A61Q 5/12* | (2006.01) | |
| *C08G 77/06* | (2006.01) | |
| *C08L 83/04* | (2006.01) | |
| *A61Q 5/00* | (2006.01) | |
| *A61K 8/898* | (2006.01) | |
| *C08G 59/16* | (2006.01) | |
| *C08G 59/30* | (2006.01) | |
| *C08G 59/68* | (2006.01) | |
| *D06M 15/643* | (2006.01) | |
| *C08L 83/10* | (2006.01) | |
| *C08L 83/12* | (2006.01) | |
| *C08G 77/16* | (2006.01) | |
| *C08G 77/388* | (2006.01) | |
| *C08G 77/445* | (2006.01) | |

(52) U.S. Cl.
CPC ................ *C08G 77/04* (2013.01); *A61K 8/06* (2013.01); *A61K 8/891* (2013.01); *A61K 8/898* (2013.01); *A61Q 5/00* (2013.01); *A61Q 5/02* (2013.01); *A61Q 5/06* (2013.01); *A61Q 5/12* (2013.01); *C08G 59/1472* (2013.01); *C08G 59/306* (2013.01); *C08G 59/686* (2013.01); *C08G 77/06* (2013.01); *C08L 83/04* (2013.01); *C08L 83/10* (2013.01); *C08L 83/12* (2013.01); *D06M 15/643* (2013.01); *A61K 2800/54* (2013.01); *C08G 77/14* (2013.01); *C08G 77/16* (2013.01); *C08G 77/388* (2013.01); *C08G 77/445* (2013.01)

(58) Field of Classification Search
CPC ...... C08G 77/14; C08G 77/16; C08G 77/388; C08G 77/452; C08G 77/26
See application file for complete search history.

(56) References Cited

U.S. PATENT DOCUMENTS

| | | |
|---|---|---|
| 4,833,225 A | 5/1989 | Schaefer et al. |
| 4,891,166 A | 1/1990 | Schaefer et al. |
| 4,921,895 A | 5/1990 | Schaefer et al. |
| 5,096,979 A | 3/1992 | O'Lenick, Jr. |
| 5,153,294 A | 10/1992 | O'Lenick, Jr. |
| 5,160,297 A | 11/1992 | O'Lenick, Jr. |
| 6,240,929 B1 | 6/2001 | Richard et al. |
| 6,242,554 B1 | 6/2001 | Busch et al. |
| 6,403,061 B1 | 6/2002 | Candau et al. |
| 6,730,766 B2 | 5/2004 | Schattenmann et al. |
| 7,041,767 B2 | 5/2006 | Lange et al. |
| 7,217,777 B2 | 5/2007 | Lange et al. |
| 2002/0103094 A1 | 8/2002 | Masschelein et al. |
| 2006/0223939 A1 | 10/2006 | Lange et al. |
| 2006/0235181 A1 | 10/2006 | Lange et al. |
| 2007/0041929 A1 | 2/2007 | Torgerson et al. |
| 2007/0286837 A1 | 12/2007 | Torgerson et al. |
| 2008/0292575 A1 | 11/2008 | Uehara |
| 2012/0289649 A1 | 11/2012 | Wagner et al. |
| 2013/0259820 A1 | 10/2013 | Snyder et al. |
| 2015/0010487 A1 | 1/2015 | Snyder et al. |
| 2015/0011449 A1 | 1/2015 | Snyder et al. |
| 2015/0037273 A1* | 2/2015 | Wagner .................. C08L 83/10 424/70.122 |
| 2015/0056155 A1* | 2/2015 | Wagner .................. C08L 83/10 424/70.122 |
| 2015/0003420 A1 | 4/2015 | Snyder et al. |
| 2015/0093421 A1 | 4/2015 | Snyder et al. |
| 2015/0299400 A1* | 10/2015 | Wagner .................. C08L 83/10 424/70.12 |

FOREIGN PATENT DOCUMENTS

| | | |
|---|---|---|
| CN | 101198311 | 7/2012 |
| WO | 2011064255 | 6/2011 |
| WO | 2013148629 | 10/2013 |
| WO | 2013148635 | 10/2013 |
| WO | 2013148935 | 10/2013 |

\* cited by examiner

*Primary Examiner* — Margaret G Moore

(74) *Attorney, Agent, or Firm* — Dilworth & Barrese, LLP

(57) ABSTRACT

The present invention provides a polyorganosiloxane compound having a low viscosity, a process for the manufacture of such polyorganosiloxane compounds, polyorganosiloxane compositions comprising said polyorganosiloxane compound and another polyorganosiloxane compound which is different from the polyorganosiloxane compound, aqueous emulsions comprising the polyorganosiloxane compound, and a method of surface treatment using the polyorganosiloxane compound.

27 Claims, No Drawings

LOW VISCOSITY POLYORGANOSILOXANES COMPRISING QUATERNARY AMMONIUM GROUPS, METHODS FOR THE PRODUCTION AND THE USE THEREOF

FIELD OF THE INVENTION

The present invention provides a polyorganosiloxane compound having a low viscosity and comprising quaternary ammonium groups, terminal ester groups and at least one functional organic group, comprising one or more hydroxyl groups and at least one functional group selected from an ester group, an ether group and an amino group, having a certain molar ratio of the quaternary ammonium groups and the terminal ester groups, a process for the manufacture of such polyorganosiloxane compounds, polyorganosiloxane compositions comprising said polyorganosiloxane compound and another polyorganosiloxane compound which is different from the polyorganosiloxane compound, aqueous emulsions comprising the polyorganosiloxane compound, and a method of surface treatment using the polyorganosiloxane compound.

BACKGROUND OF THE INVENTION

Silicone quats (silicones containing quaternary ammonium groups optionally containing polyorganosiloxane substituents) are known to be highly substantive, that is, they have a high ability to bind to carriers such as, for example, fibers, keratin substances, such as hairs etc. U.S. Pat. No. 4,891,166 describes the reaction of α,ω-diepoxides with tertiary amines in the presence of acids yielding α,ω-diquaternary siloxanes. They can be used for hair care purposes. U.S. Pat. No. 4,891,166 describes tetra alkyl derivatives as well as aromatic imidazolinium derivatives.

The reaction of α,ω-diepoxides with di-tertiary amines in the presence of acids yields polyloop polyquaternary polyorganosiloxanes (U.S. Pat. No. 4,833,225). The advantage of these materials is an improved wash off resistance from hair.

The reaction of α,ω-diepoxides with dimethylamine in the presence of acids yields polyloop polyquaternary polyorganosiloxanes having one quat group between the siloxane blocks is disclosed in U.S. Pat. No. 6,730,766.

Polyquaternary imidazolinium derivates are described in U.S. Pat. No. 6,240,929. These cationic compounds possess an improved compatibility with anionic surfactants in cosmetic formulations.

The incorporation of alkylene oxide moieties in silicone quats is to further increase the hydrophilicity.

Silicone quats containing quat groups as well as polyethylene oxide moieties in side chains are described in U.S. Pat. No. 5,098,979, U.S. Pat. No. 5,153,294 and U.S. Pat. No. 5,166,297. The substantivity of the materials, i.e. their ability to bind to carriers, is relatively low.

Silicone based block copolymers containing quat functions that also include polyether moieties are described in U.S. Pat. No. 7,217,777, U.S. Pat. No. 7,041,767 and US 2002/0103094 A. The alkylene oxide structures are incorporated into the block copolymer as α,ω-difunctional moieties.

U.S. Pat. No. 6,242,554 describes α,ω-difunctional siloxane derivatives containing one polyether and one quat function separated from each other. The substantivity of these monoquats is insufficient.

U.S. Pat. No. 4,921,895 describes blends of polyethersiloxanes and quaternary ammonium groups containing siloxane block copolymers for textile finishing purposes. Here, the usage of the polyethersiloxane improves the finished goods and hydrophilicity.

US 2007/0286837, US 2007/0041929, US 2008/0292575 and CN 101198311 describe combinations between silicone quats having a siloxane chain length of greater than 200 D-units and is a second silicone for hair conditioning purposes. One possible choice of the second silicone is the choice of silicone polyethers derived from ethylene oxide or propylene oxide or mixtures thereof. Specific structures are not given.

Low viscosity polyorganosiloxanes comprising quaternary ammonium groups are described in WO 2013/148629. The incorporation of alkylene oxide moieties into low viscosity polyorganosiloxanes comprising quaternary ammonium groups is described in WO 2013/148935 and WO 2013/148635.

The advantage of these low viscosity polymers is the improved dispersibility in liquids, i.e. water. US 2013/0259820, US 2015/0093421, US 2015/0093420 describe the usage of low viscosity polyorngnosiloxanes comprising quaternary ammonium groups and alkylene oxide groups in conditioners.

US 2015/0010487 and US 2015/0011449 describe the usage of low viscosity polyorganosiloxanes comprising quaternary ammonium groups and alkylene oxide groups in shampoos.

US 2006/0223939 and US 2006/0235181 describe polyorganosiloxanes comprising quaternary ammonium groups and different hydrophilic moieties. A moiety of the structure —$CH_2CH(OH)CH_2OCH_2CH(OH)CH_2OCH_2CH(OH)CH_2$— is disclosed. Instructions for the incorporation of this desirable moiety, which is based on renewable raw materials and readily biodegradable, into low viscosity polyorganosiloxanes comprising quaternary ammonium groups are not give.

U.S. Pat. No. 6,403,061 describes UV photo-protecting W/O emulsions. Certain poly(oxyalkylated) silicones are used as W/O emulsifiers to stabilize the formulations. Disadvantage is that these poly(oxyalkylated) silicones itself and/or low molecular weight poly(oxyalkylated) monomer traces and/or by-products are suspected to have potentially a skin sensitizing effect in cosmetic applications. Furthermore hydrophilicity of such poly(oxyalkylated) silicones in some instances is not high enough to provide superior dispersibility in water.

None of the above prior art disclosures describes a straight forward methodology for the preparation of low viscosity polyorganosiloxanes comprising quaternary ammonium groups and additional functional organic groups, comprising one or more hydroxyl groups and at least one functional group selected from an ester group, an ether group and an amino group. Low viscosity materials comprising additional strongly hydrophilic hydroxylated moieties would further improve the dispersibility in water, thus reducing the system requirements during the formulation process.

SUMMARY OF THE INVENTION

The present invention provides for a polyorganosiloxane compound comprising: A polyorganosiloxane compound comprising:
- at least one polyorganosiloxane group (a),
- at least one quaternary ammonium group (b),
- at least one terminal ester group (c), at least one functional organic group (d), comprising one or more hydroxyl groups and at least one functional group selected from an ester group, an ether group and an amino group, and wherein the molar ratio of the quaternary ammonium groups (b) and the terminal ester groups (c) is less than 100:15.

The polyorganosiloxane compound is a low viscosity silicone (oligomeric or polymeric siloxane) comprising one or more kind of repeating units as specified herein further.

The present invention further provides a process for the manufacture of such polyorganosiloxane compounds, polyorganosiloxane compositions comprising the polyorganosiloxane compound, aqueous emulsions comprising the polyorganosiloxane compound, and a method of surface treatment using the polyorganosiloxane compound.

DETAILED DESCRIPTION OF THE INVENTION

The present invention provides for low viscosity polyorganosiloxanes comprising quaternary ammonium groups, their manufacture and the use of the materials.

Surprisingly, polyorganosiloxanes comprising quaternary ammonium groups possessing a low viscosity can be accomplished by the preparation of polyorganosiloxane compounds comprising quaternary ammonium groups, terminal ester groups and further functional organic groups, comprising one or more hydroxyl groups and at least one functional group selected from an ester group, an ether group and an amino group.

The polyorganosiloxane compounds according to the invention preferably are linear copolymer compounds that comprise the above functional groups (a), (b), (c) and (d) in at least two repeating units, with at least part of the terminal groups being terminal ester groups that result from the use of monofunctional organic acids as chain stoppers.

Formally the polyorganosiloxane compounds have -(G-D)$_x$-, preferably [—CH$_2$—X—CH$_2$-D-]$_x$-chains (wherein X is as defined below) with G, preferably —CH$_2$—X—CH$_2$—, resulting in particular from a difunctional alkylating compound (such as diepoxides, or di(halogenalkyl) compounds) and D resulting in particular from compounds that can be alkylated (such as tertiary diamines). These chains are at least partially terminated by ester groups, in particular, ester groups that result from the reaction of epoxy groups and mono acids. x is usually >1, but may also include the case wherein x=1.

In a preferred embodiment of the invention the polyorganosiloxane compound has terminal ester groups (c) which are selected from carboxylic acid ester groups, sulfonic acid ester groups, sulfuric acid ester groups, and phosphoric acid mono- or diester groups. Most preferably the terminal ester groups are carboxylic acid ester groups.

In a further preferred embodiment of the invention the functional organic group (d) is a divalent organic group having up to 60 carbon atoms, comprising at least one hydroxyl group and at least functional group selected from an ester group, an ether group and an amino group. More preferably the functional organic group (d) is a divalent organic group having up to 60 carbon atoms, comprising at least one hydroxyl group, and at least one ether group, and optionally at least one ester group and/or amino group.

The functional organic group (d) is preferably generated by the use of a corresponding difunctional alkylating compound, preferably di(halogenalkyl) compounds, having such functional organic group (d). The hydroxy group of the functional organic group (d) is preferably obtained by the use of glycerol or polyglycerol moieties.

In a preferred embodiment of the invention the polyorganosiloxane compound, comprises at least one unit of the formula (I):

[—CH$_2$—X—CH$_2$-D-] (I).

Such type of compounds having the two —CH2- groups in the repeating unit of formula (I) result in particular from the quaternizing reaction of amino compounds with alkylating compounds such as in particular diepoxides or halogenmethylen compounds, which in both case form methylene ammonium groups (—CH$_2$—N$^+$). Preferably there is at least one repeating unit of formula (I), more preferably there are at least two repeating units of formula (I).

In formula (I): D is selected from quaternary ammonium units, such as:

—N$^+$R$_2$—, resulting for example from the reaction of secondary amines with alkylating compounds which are subsequently subjected to quaternizing reaction by reaction with further alkylating compounds, —N$^+$R$_2$—Y—N$^+$R$_2$—, resulting for example from the reaction of ditertiary the minor compounds with alkylating compounds, a saturated or unsaturated mono or diquaternary heterocycle of the formulae

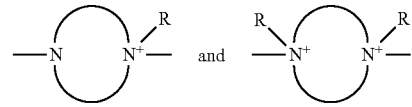

e.g. moieties derived from piperazine moieties, and an aromatic ammonium heterocycle of the formula

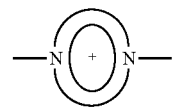

e.g. moieties resulting from nitrogen containing heterocycles,

X is at least one group X$^1$ and at least one group X$^2$, that is, at least one group X$^1$ and at least one group X$^2$ is present, wherein X$^1$ is selected from a difunctional organic group, comprising one or more hydroxyl groups and at least one functional group selected from an ester group, an ether group and an amino group, and wherein said group X$^1$ does not comprise a polydiorganosiloxane group, preferably X$^1$ is an optionally substituted difunctional organic group having up to 40 carbon atoms, preferably up to 30 carbon atoms and having at least one, preferably at least two, more preferably at least three hydroxyl groups, and preferably at least one ether group.

X$^2$ is selected from a difunctional organic group, comprising at least one polydiorganosiloxane group, X$^2$ is preferably an optionally substituted difunctional organic group having up to 40 carbon atoms, preferably up to 30 carbon atoms (not including the carbon atoms of the polydiorganosiloxane moiety) and preferably having at least one heteroatom selected from O, N, preferably O, and preferably having at least one hydroxyl group (again not taking the atoms of the polydiorganosiloxane moiety into account).

R is selected from monovalent organic groups having up to 22 carbon atoms and optionally one or more heteroatoms. Preferably R is selected from C1-C6 alkyl groups, more preferably a methyl group.

Y is selected from a difunctional organic group which may comprise one or more heteroatoms.

Preferably Y is an optionally substituted difunctional organic group having up to 40 carbon atoms, preferably up to 30 carbon atoms, and optionally at least one heteroatom, preferably selected from N or O. Y is preferably selected from a C1-C10 alkyl groups, which optionally may have one or two substituents such as hydroxy groups, and polyalkylene oxide moieties, preferably comprising ethylene and/or propylene oxide moieties, having up to 40 carbon atoms.

In a still further embodiment of the invention the polyorganosiloxane compound the units of the formula (I) are selected from formula (Ia):

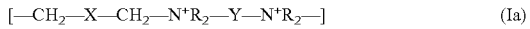

[—$CH_2$—X—$CH_2$—$N^+R_2$—Y—$N^+R_2$—]   (Ia)

wherein X, R and Y are as defined above. These embodiments result in particular from quarternizing reactions with ditertiary amino compounds.

In a further preferred embodiment the polyorganosiloxane compound comprises units of the formula (Ia) which are selected from:

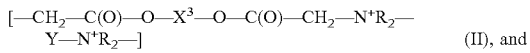

[—$CH_2$—C(O)—O—$X^3$—O—C(O)—$CH_2$—$N^+R_2$—Y—$N^+R_2$—]   (II), and

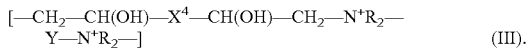

[—$CH_2$—CH(OH)—$X^4$—CH(OH)—$CH_2$—$N^+R_2$—Y—$N^+R_2$—]   (III).

Polyorganosiloxane compounds comprising units of the formula (II) result in particular from the reaction of difunctional halogen (in particular chlorine)methylester terminated compounds, which are preferably derived from the reaction of diepoxides with chloro acetic acid, with di-tertiary amino compounds.

Polyorganosiloxane compounds comprising units of the formula (III) result in particular from the reaction of diepoxides with di-tertiary amino compounds.

In a preferred embodiment the polyorganosiloxane compounds of the invention comprise both units of formula (II) and (III), i.e. are obtained from the reaction of di-tertiary amino compounds with diepoxides and difunctional halogen (in particular chlorine)methylester terminated compounds.

In formulas (II) and (III) above, R and Y are as defined above, and $X^3$ is selected from $X^{31}$ and $X^{32}$, wherein $X^{31}$ is selected from a difunctional optionally substituted, preferably substituted organic group, comprising one or more hydroxyl groups and at least one functional group selected from an ester group, an ether group and an amino group, and wherein said group $X^{31}$ does not comprise a polydiorganosiloxane group, preferably $X^{31}$ is a hydroxy-substituted difunctional organic, preferably aliphatic organic group having up to 40, preferably up to 30 carbon atoms, having at least one, preferably at least two, more preferably at least three hydroxyl groups, and preferably at least one ether group, preferably more than one ether group.

$X^{32}$ is selected from an optionally substituted difunctional organic group, comprising at least one polydiorganosiloxane group, $X^{32}$ is preferably an optionally substituted difunctional organic group having up to 40 carbon atoms, preferably up to 30 carbon atoms (not including the carbon atoms of the polydiorganosiloxane moiety) and optionally having at least one heteroatom selected from O, N, preferably O, and optionally having at least one hydroxyl group (again not taking the atoms of the polydiorganosiloxane moiety into account). The group $X^{32}$ is preferably resulting from the reaction of diepoxide-terminated polydiorganosiloxane compounds that are subsequently reacted with chloro acetic acid, forming di(chloromethyl)-terminated polydiorganosiloxane compounds which can be subjected to quarternizing reaction with for example ditertiary amino compounds.

and $X^4$ is selected from $X^{41}$ and $X^{42}$, wherein $X^{41}$ is selected from a difunctional preferably substituted organic group, preferably comprising up to 40, more preferably thirty carbon atoms, comprising one or more hydroxyl groups and at least one functional group selected from an ester group, an ether group and an amino group, preferably an ether group and wherein said group $X^{41}$ does not comprise a polydiorganosiloxane group, $X^{42}$ is selected from a difunctional organic group, comprising at least one polydiorganosiloxane group, $X^4$ is preferably an optionally substituted difunctional organic group having up to 40 carbon atoms, preferably up to 30 carbon atoms (not including the carbon atoms of the polydiorganosiloxane moiety) and optionally having at least one heteroatom selected from O, N, preferably O, and optionally having at least one hydroxyl group (again not taking the atoms of the polydiorganosiloxane moiety into account).

Preferably the polyorganosiloxane compound according to the invention, comprises units of the formula (II) and of the formula (III).

In a preferred embodiment of the invention $X^{41}$ is selected from a group of formula (IV):

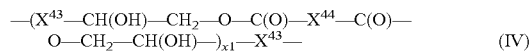

—($X^{43}$—CH(OH)—$CH_2$—O—C(O)—$X^{44}$—C(O)—O—$CH_2$—CH(OH)—)$_{x1}$—$X^{43}$—   (IV)

wherein $X^{43}$ is selected from a difunctional organic group, comprising one or more hydroxyl groups and at least one functional group selected from an ester group, an ether group and an amino group, and $X^{44}$ is selected from an optionally substituted difunctional organic group, optionally comprising one or more heteroatoms, and x1 is ≥1.

Polyorganosiloxane compounds according to the invention comprising groups of formula (IV) are obtained in particular by reacting diepoxides with dicarboxylic acids with ring opening of the epoxy group forming ester groups. Such epoxy terminated ester, in particular polyester, oligomers are subsequently subjected to quaternising reaction with in particular ditertiary-amines.

In another preferred embodiment $X^{41}$ is selected from a group of formula (V):

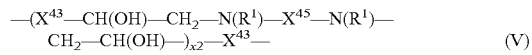

—($X^{43}$—CH(OH)—$CH_2$—N($R^1$)—$X^{45}$—N($R^1$)—$CH_2$—CH(OH)—)$_{x2}$—$X^{43}$—   (V)

wherein $X^{43}$ is as defined above, $X^{45}$ is selected from a difunctional, optionally substituted, organic group, having up to 40, preferably up to 30 carbon atoms, optionally comprising one or more heteroatoms, $R^1$ is selected in particular from hydrogen and a C1-C6 alkyl group, and x2 is ≥1. Polyorganosiloxane compounds according to the invention comprising groups of formula (V) are prepared in particular by reacting diepoxides with diamino compounds, resulting in particular epoxy terminated amino oligomers which are subsequently subjected to quaternising reaction with in particular ditertiary-amines.

In another preferred embodiment $X^{31}$ is selected from a group of formula (VI):

—CH$_2$—CH(OH)—(X$^{33}$—CH(OH)—CH$_2$—O—C(O)—X$^{34}$—C(O)—O—CH$_2$—CH(OH)—)$_{x3}$—X$^{33}$—CH(OH)—CH$_2$— (VI)

wherein $X^{33}$ is selected from a difunctional optionally substituted organic group, having up to 40 preferably up to 30 carbon atoms, comprising one or more hydroxyl groups and at least one functional group selected from an ester group, an ether group and an amino group, preferably X33 comprises at least one ether group, $X^{34}$ is selected from a difunctional optionally substituted organic group, comprising up to 40, preferably up to 30 carbon atoms and optionally comprising one or more heteroatoms, preferably comprising one or more hydroxy groups, and x3 is ≥1.

Polyorganosiloxane compounds according to the invention comprising groups of formula (VI) are obtained in particular by reacting diepoxides with dicarboxylic acids, wherein the epoxy-terminated (poly)ester oligomers simultaneously or subsequently are reacted with chloro acetic acid subsequently are subjected to quaternising reaction with in particular ditertiary amino compounds.

In another preferred embodiment $X^{31}$ is selected from a group of formula (VII):

—CH$_2$—CH(OH)—(X$^{33}$—CH(OH)—CH$_2$—N(R$^1$)—X$^{45}$—N(R$^1$)—CH$_2$—CH(OH)—)$_{x4}$—X$^{33}$—CH(OH)—CH$_2$— (VII)

wherein $X^{33}$, $X^{45}$ and $R^1$ are as defined above, and x4 is ≥1. Polyorganosiloxane compounds according to the invention comprising groups of formula (VII) are obtained in particular by reacting diepoxides with diamino compounds, reacting the resulting epoxy-terminated polyamino compound subsequently with chloro acteic acid subsequently are subjected to quaternising reaction with in particular ditertiary amino compounds.

In a still more preferred embodiment of the invention formula (I) is selected from the group of the following formula:

[—CH$_2$—C(O)—O—(CH$_2$CH(OH)CH$_2$O)$_3$—C(O)—CH$_2$—N$^+$R$_2$—Y—N$^+$R$_2$—] (II-a).

Polyorganosiloxane compounds according to the invention comprising groups of formula (II-a) are obtained in particular by reacting

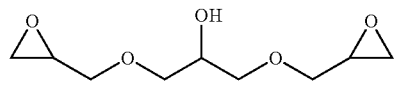 [SMILES: OC(COCC1CO1)COCC1CO1]

with chloro acetic acid to form:

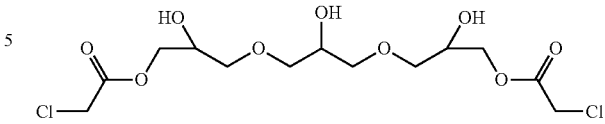

which is subsequently reacted in quaternising reaction with in particular ditertiary amino compounds. This is a particular preferred embodiment of the invention.

In a still more preferred embodiment of the invention formula (I) is selected from the group of the following formula:

[—CH$_2$—CH(OH)—CH$_2$—O—CH$_2$—CH(OH)—CH$_2$—O—CH$_2$—CH(OH)—CH$_2$—N$^+$R$_2$—Y—N$^+$R$_2$—] (III-a).

Polyorganosiloxane compounds according to the invention comprising groups of formula (III-a) are obtained in particular by subjecting

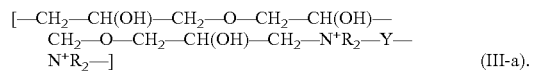

directly to quaternising reaction with in particular ditertiary amino compounds.

In a still more preferred embodiment of the invention formula (I) is selected from the group of the following formula:

[—CH$_2$—C(O)—O—CH$_2$—CH(OH)—(X$^{33}$—CH(OH)—CH$_2$—O—C(O)—X$^{34}$—C(O)—O—CH$_2$—CH(OH)—)$_{x3}$—X$^{33}$—CH(OH)—CH$_2$—O—C(O)—CH$_2$—N$^+$R$_2$—Y—N$^+$R$_2$—] (II-b)

wherein $X^{33}$ is a moiety of the following formula:

—CH$_2$—O—CH$_2$—CH(OH)—CH$_2$—O—CH$_2$— and wherein $X^{34}$ is a moiety of the following formula:

—CH(OH)—CH(OH)— and wherein R and Y are each as defined above.

Polyorganosiloxane compounds according to the invention comprising groups of formula (I-b) are obtained in particular by subjecting

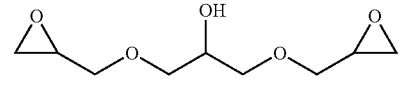 [SMILES: OC(COCC1CO1)COCC1CO1]

1,3-bis(oxran-2-ylmethoxy)propan-2-ol to the reaction with tartaric acid:

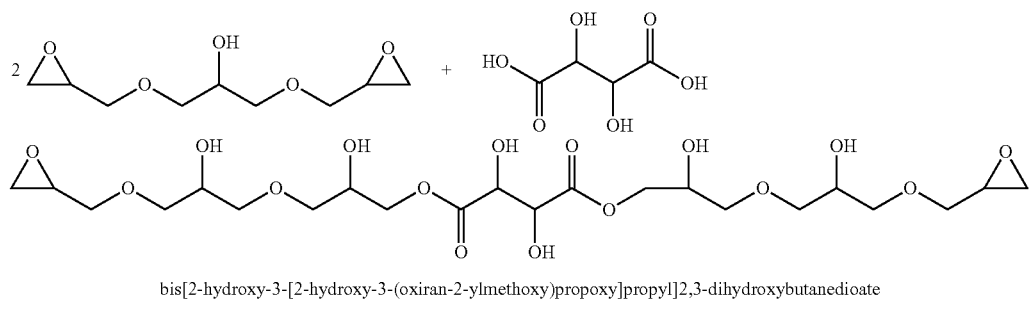

bis[2-hydroxy-3-[2-hydroxy-3-(oxiran-2-ylmethoxy)propoxy]propyl]2,3-dihydroxybutanedioate (this compound can be also directly subjected to quaternising reaction with in particular ditertiary amino compounds). which is subsequently reacted with chloro acetic acid to form:

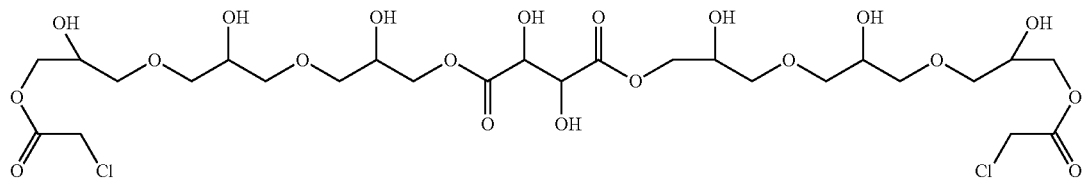 [SMILES: O=C(CCl)OCC(O)COCC(O)COCC(O)COC(=O)C(O)C(O)C(=O)OCC(O)COCC(O)COCC(O)COC(=O)CCl]

which is subsequently subjected to quaternising reaction with in particular ditertiary amino compounds.

In a further preferred embodiment the group $X^1$ (appearing in the definition of formula (I)) is of the formula (VIII):

-A-E-A'- (VIII)

wherein A and A' each are independently from each other and are each selected from the group consisting of a single bond and a divalent organic group having up to 10 carbon atoms and optionally one or more hetero atoms, and E is selected from the group of the formulas $E^1$:

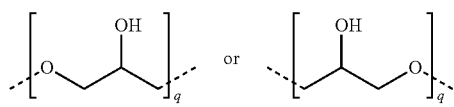

wherein q is independently from each other ≥1, preferably q is 3, and ------ denotes a single bond, (an example of a repeating unit comprising such a group

-A-E-A'- (VIII)

comprising such 1-oxy-propin-2-ol units are represented e.g. by:

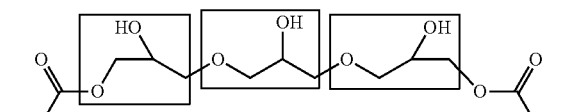

wherein q is 3 accordingly).

a group of the formula $E^2$:

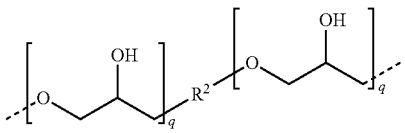

wherein ------ denotes a single bond, $R^2$ is an optionally substituted, bivalent straight chain, cyclic aliphatic and/or branched and/or aromatic hydrocarbon residue with up to 40 carbon atoms, which may contain one or more heteroatoms selected from O and N, and wherein each q is independently from each other ≥1, preferably each q is 3, (an example of such group E2 is for example formed by subjecting a compound of the formula

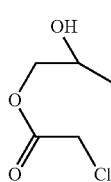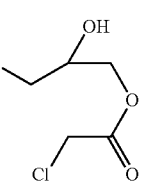

which is obtained as described above. Considering formula (VIII)) A would be —C(O)—, q=3; R2 would be

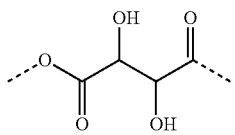

(with . . . denoting a single bond), and A' would be —O—C(O)—).

a group of the formula $E^3$:

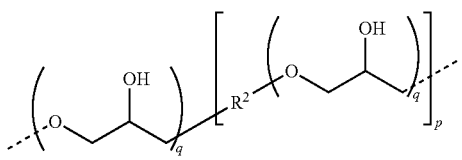

wherein ------ denotes a single bond, $R^2$ is as defined above, each q independently from each other is ≥1, preferably 3, and p is >1.

(An example of a compound having such structure would be obtained e.g. from a compound of formula:

In the formula $$-A-E-A'- \qquad \text{(VIII)}$$

it should be clear that A and E or A' and E are not bond via two hetero atoms.

In a further preferred embodiment in the polyorganosiloxane compound of the invention according the group $X^1$ is of the formula (VIII) as defined above and E is a group $E^4$ of formula:

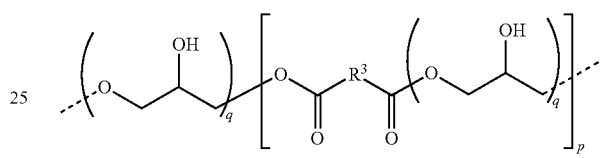

wherein ------ denotes a single bond, $R^3$ is an optionally substituted, bivalent straight chain, cyclic aliphatic and/or branched and/or aromatic hydrocarbon residue with up to 38 carbon atoms, which may contain one or more heteroatoms selected from O and N, and each q is ≥1, and may be the same or different, p is ≥1, preferably each q is 3, again with the proviso that A and E or A' and E are not bond via two hetero atoms.

E3

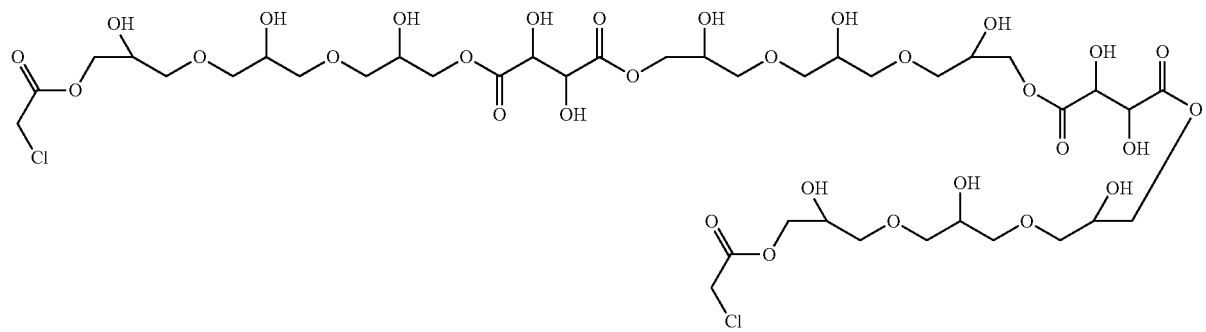

wherein p=2. Such compounds result from oligomerisation reaction of

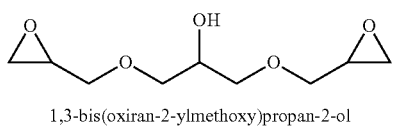 [SMILES: OC(COCC1CO1)COCC1CO1]

1,3-bis(oxiran-2-ylmethoxy)propan-2-ol with tartaric acid and termination with chloro acetic acid).

In a preferred embodiment the functional organic group (d) has the formula (I):

$$-A-E-A'- \qquad \text{(I)}$$

with E being $E^2$:

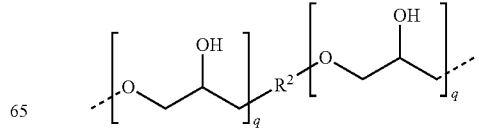

wherein ------ denotes a single bond, R² is an optionally substituted, bivalent straight chain, cyclic and/or branched aliphatic and/or aromatic hydrocarbon residue with up to 40 carbon atoms, which may contain one or more heteroatoms selected from O and N, wherein each q is ≥1, most preferably 3, and may be the same or different, with the proviso that A and E or A' and E are not bond via two hetero atoms. R² can be in particular a bivalent straight chain aliphatic hydrocarbon residue with up to 10 carbon atoms, preferably having at least one hydroxyl group and at least one group selected from a carbonyl and an ester group. Such groups result in particular from the reaction of a glycidol diglycidyl ether:

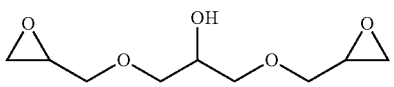 [SMILES: OC(COCC1CO1)COCC1CO1]

with an optionally substituted (preferably hydroxyl-substituted) dicarboxylic acid (with up to 20 carbon atoms) such as ethanedioic acid, propanedioic acid, butanedioic acid, pentanedioic acid, hexanedioic acid, heptanedioic acid, octanedioic acid, nonanedioic acid, decanedioic acid, undecanedioic acid, dodecanedioic acid, hexadecanedioic acid, and substituted dicarboxylic acids such as hydroxybutanedioic acid, 2-minobutanedioic acid, 2-aminopentanedioic acid, 2-hydroxypropanedioic acid, 2,3-dihydroxybutanedioic acid, (2R,6S)-2,6-diaminoheptanedioic acid, (2S,3S,4S,5R)-2,3,4,5-tetrahydmxyhexanedioic acid, oxopropanedioic acid, oxobutanedioic acid, 3-oxopentanedioic acid, 2,3,4-trihydroxypentanedioic acid, aromatic dicarboxylic acids such as benzene-1,2-dicarboxylic acid, benzene-1,3-dicarboxylic acid, benzene-1,4-dicarboxylic acid, 2-(2-carboxyphenyl)benzoic acid, 2,6-naphthaulenedicarboxylic acid, or an optionally substituted (preferably hydroxyl-substituted) diamine (with up to 20 carbon atoms).

In a still another preferred embodiment in the polyorganosiloxane compound according to the invention the functional organic group d) has the formula (VIII), as defined above, wherein E is selected from the groups of the following general formulae E⁵, E⁶ and E⁷:

-{[GLY'-GLY''-GLY']-ACD}$_{q1}$-GLY'$_{q2}$-,      E⁵:

-{[GLY'-GLY''-GLY''']-AM}$_{q1}$-GLY'$_{q2}$-, and      E⁶:

-{[GLY'-GLY''-GLY''']-AM}$_{q1}$GLY'''$_{q2}$-      E⁷:

with
q1=0 to 12,
q2>0
q1+q2=1 to 24,
GLY'=—CH₂CH(OH)CH₂O—
GLY''=—R⁴—O—
GLY'''=—CH₂CH(OH)CH₂—
ACD=—C(O)—R⁵—C(O)O—
AM=—N(R⁶)—R⁵—N(R⁶)—
R⁶ is selected from C1-C22-alkyl, C1-C22-fluoroalkyl or aryl or part of a ring system with R⁵, R⁵ is selected from a bivalent straight chain, cyclic and/or branched C2-C40 hydrocarbon residue which is optionally interrupted by —O—, trivalent N, —NR⁶—, —C(O)—, —C(S)—, and optionally substituted with —OH, or part of a ring system with R⁶, wherein R⁶ is defined as above, R⁴ is selected from a bivalent straight chain, cyclic and/or branched and/or aromatic C2-C40 hydrocarbon residue which is optionally interrupted by —O—, —C(O)—, —C(S)—, and optionally substituted with —OH.

This leads to:

—{[CH₂CH(OH)CH₂O—R⁴—O—CH₂CH(OH)
CH₂O—]—C(O)—R⁵—C(O)O—}$_{q1}$—(CH₂CH
(OH)CH₂O)$_{q2}$—,      E⁵:

—{[—CH₂CH(OH)CH₂O—R⁴—O—CH₂CH(OH)
CH₂—]—N(R⁶)—R⁵—N(R⁶)—}$_{q1}$—(CH₂CH
(OH)CH₂O)$_{q2}$—, and      E⁶:

—{[—CH₂CH(OH)CH₂O—R⁴—O—CH₂CH(OH)
CH₂—]—N(R⁶)—R⁵—N(R⁵)—}$_{q1}$—(CH₂CH
(OH)CH₂)$_{q2}$—.      E⁷:

In a preferred embodiment of the polyorganosiloxane compounds according to the invention the at least one polyorganosiloxane group (a) is of the general formula:

—K—S—K—      (IX)

with
S is a siloxane moiety of the formula (X):

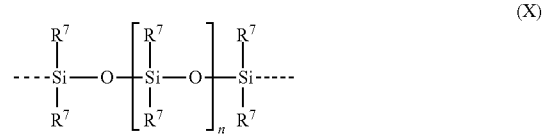

(X)

wherein ------ denotes a single bond to K,
wherein R⁷ is selected from C1-C22-alkyl, C1-C22-fluoroalkyl or aryl, n is 0 to 1000, and these can be identical or different if several S Groups are present in the polyorganosiloxane compound,
K is selected from a bivalent or trivalent straight chain, cyclic and/or branched C2-C40 hydrocarbon residue which is optionally interrupted by —O—, —NH—, trivalent N, —NR⁷—, —C(O)—, —C(S)—, and optionally substituted with —OH, wherein R⁷ is defined as above, whereby the residues K can be identical or different from each other.

Polyorganosiloxane groups of the general formula:

—K—S—K—      (IX)

are introduced into the polyorganosiloxane compounds according to the invention in particular with diepoxy-terminated polyorganosiloxanes, e.g. of formula:

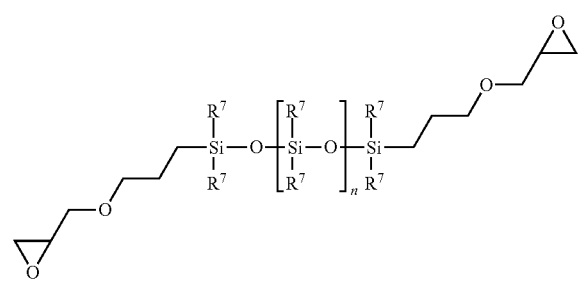

which are in turn obtained by hydrosilylation reaction of SiH-terminated polydiorganosiloxanes with

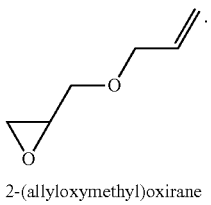

2-(allyloxymethyl)oxirane

It is also possible to first subject the diepoxides of formula:

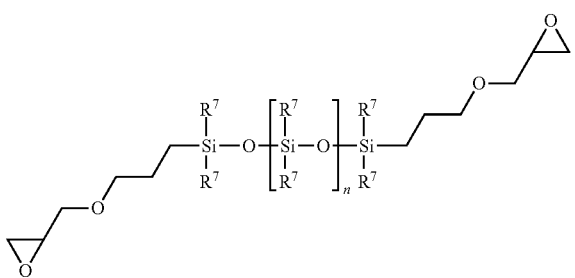

to initial oligomerization reactions, e.g. with difunctional compounds such as dicarboxylic acids or diamino compounds, and than for example to subject the resulting epoxy-terminated oligomers to quaternising reaction.

In a preferred embodiment the polyorganosiloxane compounds comprise units of formula.

[—CH$_2$—X—CH$_2$-D-]  (I)

wherein D is as defined above and X is X$^2$ having the formula (IX):

—K—S—K—  (IX)

as defined before.

In a further preferred embodiment in the polyorganosiloxane compounds according to the invention the quaternary ammonium group (b) is selected from the general formulas:

—N$^+$R$_2$—

—N$^+$R$_2$—Y—N$^+$R$_2$—, a saturated or unsaturated mono or diquaternary heterocycle of the formulae

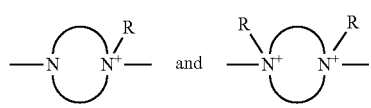

and an aromatic ammonium heterocycle of the formula

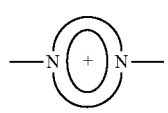

wherein R is as defined above, and wherein the free valencies at the nitrogen atoms are bound to carbon atoms, and Y is as defined above.

In a further preferred embodiment in the polyorganosiloxane compound according to the invention comprising unit of the formula (I):

[—CH$_2$—X—CH$_2$-D-]  (I)

X is a group X$^1$ of the formula (VIII):

-A-E-A'-  (VIII)

wherein A and A' are independently selected from the following groups:
a single bond,
—C(O)—
—O—C(O)—
—C(O)—O—
—CH$_2$—C(O)—O—
—O—C(O)—CH$_2$—
—CH$_2$CH$_2$—C(O)—O—
—O—C(O)—CH$_2$—CH$_2$—
—CH$_2$CH$_2$CH$_2$—C(O)—O—
—O—C(O)—CH$_2$—CH$_2$CH$_2$—
—CH$_2$CH$_2$—O—
—O—CH$_2$CH$_2$—
—C(O)—CH$_2$—
—CH$_2$—C(O)—
—C(O)—CH$_2$CH$_2$—
—CH$_2$CH$_2$—C(O)—
—C(O)—CH$_2$CH$_2$CH$_2$—
—CH$_2$CH$_2$CH$_2$—C(O)—
—CH$_2$CH$_2$—, and
—N(R$^6$)—R$^5$—N(R$^6$)— with R$^6$ and R$^5$ as defined above.
—CH(OH)—CH$_2$—,
—O—CH$_2$—CH(OH)—,
—CH(OH)—CH$_2$—O—,
—CH$_2$—CH(OH)— and a divalent radical of the formula

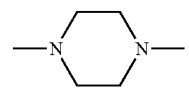

In a further preferred embodiment of the invention the polyorganosiloxane compound the terminal ester groups (c) are selected from the group of:
—OC(O)—Z
—OS(O)$_2$—Z
—OS(O$_2$)O—Z
—OP(O)(O—Z)OH and
—OP(O)(O—Z)$_2$
wherein Z is selected from monovalent organic residues having up to 40 carbon atoms, optionally comprising one or more hetero atoms.

In a still further preferred embodiment of the invention the polyorganosiloxane compounds are of the general formulas (Ib) and (Ic):

M-X$^5$—[—(—N$^+$R$_2$—Y—N$^+$R$_2$)—X$^5$—]$_m$—[—(NR$^2$-A-E-A'-NR$^2$)—X$_5$—]$_k$-M  (Ib)

M-X$^5$—[—(—N$^+$R$_2$—Y—N$^+$R$_2$)—X$^5$—]$_m$—[—(N$^+$R$^2$-A-E-A'-N$^+$R$^2$)—X$_5$—]$_k$-M  (Ic)

wherein:
m is >0, preferred 0.01 to 100, more preferred 0.1 to 100, even more preferred 1 to 100, specifically 1 to 50, more specifically 1 to 20, even more specifically 1 to 10,
k is 0 or an average value of >0 to 50 preferred 1 to 20, more preferred 1 to 10, M represents a terminal group, comprising terminal ester groups selected from
—OC(O)—Z
—OS(O)$_2$—Z
—OS(O)O—Z
—OP(O)(O—Z)OH
—OP(O)(O—Z)$_2$
wherein Z is as defined above,
-A-E-A'- is as defined above,
R$^8$ is selected from hydrogen or R,
X$^5$ is a group of the formula:
—K—S—K— and -A-E-A'- or -A'-E-A-,
each as defined above, and
Y is a as defined above.

Z is preferably selected from monovalent organic residues having up to 40 carbon atoms, optionally comprising one or more hetero atoms. As will be explained in detail below these terminal ester groups result from the use of monofunctional organic acids, like carboxylic acids (—OC(O)—Z), sulfonic acids (—OS(O)$_2$—Z), sulfuric acid half ester (—OS(O$_2$)O—Z), phosphoric acid mono ester (—OP(O)(O—Z)OH), phosphoric acid diester (—OP(O)(O—Z)$_2$) in the reaction with diepoxides.

Due to the possible presence of amine groups (for example in formula (V) —(X$^{43}$—CH(OH)—CH$_2$—N(R$^1$)—X$^{45}$—N(R$^1$)—CH$_2$—CH(OH)—)$_{x2}$—X$^{43}$—) in the polyorganosiloxane compounds according to the invention, they may have protonated ammonium groups, resulting from the protonation of such amine groups with organic or inorganic acids. Such compounds are sometimes referred to as acid addition salts of the polyorganosiloxane compounds according to the invention and shall be included in the definition of the polyorganosiloxane compounds according to the invention.

In a preferred embodiment the molar ratio of the quaternary ammonium groups b) and the terminal ester groups c) is less than 100:20, even more preferred is less than 100:30 and is most preferred less than 100:50. The ratio can be determined by $^{13}$C-NMR.

The polyorganosiloxane compounds according to the invention are manufactured preferably by a process, which comprises the reaction of
(i) at least one ditertiary diamine,
(ii) at least one amino-alkylating compound, preferably comprising at least one diepoxide, and/or at least one dihalogenalkyl compound, and
(iii) at least one monofunctional organic acid,
(iv) at least one difunctional compound comprising one or more hydroxyl groups and at least one functional group selected from an ester group, an ether group and an amino group, and wherein at least one compound among compounds (i) and (i) comprises a polyorganosiloxane structural unit.

Component (iv) preferably is a difunctional compound having in terminal positions epoxy, halogen, primary, secondary, tertiary amino functions. In case it has in terminal positions epoxy, or halogenalkyl groups it acts also as amino-alkylating compound and then is covered by the definition of component (ii) as well In a further embodiment of this process in addition to the components (i) to (iv), component (v), i.e. di-primary amine or di-secondary amines are reacted in such process.

The present invention further relates to polyorganosiloxane compounds that are obtainable by the process according to the invention as described before.

A further embodiment of the present invention relates to a polyorganosiloxane composition, comprising:

A) a polyorganosiloxane compound comprising.
  at least one polyorganosiloxane group (a),
  at least one quaternary ammonium group (b),
  at least one terminal ester group (c),
  at least one functional organic group (d), comprising one or more hydroxyl groups and at least one functional group selected from an ester group, an ether group and an amino group, and
B) at least one polyorganosiloxane compound, comprising at least one terminal ester group, which polyorganosiloxane compound is different from polyorganosiloxane compound A).

In the definition of component A) it can be referred to the description of the polyorganosiloxane compounds of the invention. The polyorganosiloxane compound B) differs from the polyorganosiloxane compound A) preferably in that it does not comprise quaternary ammonium groups. Preferred polyorganosiloxane compounds B) result from the reaction of monofunctional organic acids, in particular carboxylic acids, and polyorganosiloxane containing bis-epoxides.

In the polyorganosiloxane compositions according to the invention the weight ratio of compound A) to compound B) is preferably less than 90:10. Or with other words, the content of component B) is at least 10 weight percent.

In a further preferred embodiment of the polyorganosiloxane compositions according to the invention in compound A) the molar ratio of the quaternary ammonium groups b) and the terminal ester groups c) is less than 100:10, even more preferred is less than 100:15 and is most preferred less than 100:20.

Both, the polyorganosiloxane compounds or the polyorganosiloxane compositions according to the invention preferably have a viscosity of less than 100000 mPa·s (100 Pa·s; always measured at 20° C., Brookfield, spindle 4, 12 RPM), preferably less than 90000 mPa·s, more preferably less than 80000 mPa·s.

The present invention further relates to aqueous emulsions comprising at least one polyorganosiloxane compound according to the invention and/or at least one polyorganosiloxane composition according to the invention each as defined above or below. Such aqueous emulsions preferably comprise at least 30 weight percent, preferably at least 50 weight percent, still more preferably at least 80 weight percent water based on the total weight of the emulsions.

The present invention further relates to a method of surface treatment, comprising the step of applying the polyorganosiloxane compounds, the polyorganosiloxane compositions or the aqueous emulsions thereof as defined herein, to the surface of a substrate. Any method of applying it is conceivable, e.g. simple wetting, contacting, washing, dipping, spraying, brushing, spreading operations conventionally known in the art can be referred to.

In such method preferably one of a following compositions or formulations respectively are applied: cosmetic formulations for skin and hair care, selected from Rinse-off and Leave-on conditioners, shampoos, styling gels, sprays, and pump sprays; formulations for polishing for the treatment and outfitting of hard surfaces; formulations for drying automobiles and other hard surfaces; formulations for initial outfitting of textiles and textile fibers; softener formulations comprising in addition non-ionogenic or anionic/non-ionogenic or cationic or betaine surfactants for application during or after washing textiles; laundry formulations for textile washes based upon non-ionic or anionic/non-ionic or cationic or betaine surfactants or formulations for preventing or reversing textile crumpling.

The present invention further relates to aqueous emulsions comprising at least one polyorganosiloxane according to the invention.

The present invention further relates to aqueous emulsions comprising at least one polyorganosiloxane composition according to the invention.

The present invention further relates to a method of surface treatment, comprising the step of applying the polyorganosiloxane compound according to the invention to the surface of a substrate.

The present invention further relates to a method of surface treatment, comprising the step of applying the polyorganosiloxane compositions according to the invention to the surface of a substrate.

The present invention further relates to a method of surface treatment, comprising the step of applying the aqueous emulsions according to the invention to the surface of a substrate.

The present invention further relates to a method of surface treatment, comprising the step of applying the polyorganosiloxane compounds, the polyorganosiloxane compositions or the aqueous emulsions thereof as defined herein, to the surface of a substrate, wherein one of a following compositions or formulations respectively are applied: cosmetic formulations for skin and hair care, selected from Rinse-off and Leave-on conditioners, shampoos, styling gels, sprays, and pump sprays; formulations for polishing for the treatment and outfitting of hard surfaces; formulations for drying automobiles and other hard surfaces; formulations for initial outfitting of textiles and textile fibers; softener formulations comprising in addition non-ionogenic or anionic/non-ionogenic or cationic or betaine surfactants for application during or after washing textiles; laundry formulations for textile washes based upon non-ionic or anionic/non-ionic or cationic or betaine surfactants or formulations for preventing or reversing textile crumpling.

The present invention further relates to cosmetic compositions or formulations, comprising at least one polyorganosiloxane compound according to the invention, and/or at least one polyorganosiloxane composition according to the invention, and/or at least one aqueous emulsion according to the invention. Cosmetic compositions or formulations according to the invention, are for example selected from the group consisting of skin care compositions, hair care compositions, selected from conditioners, including rinse off and leave on conditioners, shampoos, including anionic shampoo, cationic shampoo, non-ionic shampoo and amphoteric shampoo, hair setting formulations, clear rinse-off hair setting agents, hair foam setting formulations, hair mousses, hair styling gels, hair styling sprays, hair dyes, hair color products, and pump sprays, hair bleaches, waving products, hair straighteners, deodorants, antiperspirants, antiperspirant/deodorants, shaving products, skin lotions, moisturizers, toners, bath products, cleansing products, manicure products, protective creams, color cosmetics and other cosmetic formulations where silicone components have been conventionally added.

The present invention further relates to formulations for the treatment of hard surfaces, comprising at least one polyorganosiloxane compound according to the invention, and/or at least one polyorganosiloxane composition according to the invention, and/or at least one aqueous emulsion according to the invention.

The present invention further relates to formulations for the treatment of textiles and textile fibers comprising at least one polyorganosiloxane compound according to the invention, and/or at least one polyorganosiloxane composition according to the invention, and/or at least one aqueous emulsion according to the invention. Formulation or the treatment of textiles and textile fibers include for example: formulations for initial outfitting of textiles and textile fibers, softener formulations, optionally comprising in addition non-ionogenic or anionic/non-ionogenic or cationic or betaine surfactants for application during or after washing textiles.

The present invention further relates to laundry formulations comprising at least one polyorganosiloxane compound according to the invention, and/or at least one polyorganosiloxane composition according to the invention, and/or at least one aqueous emulsion according to the invention.

FURTHER PREFERRED EMBODIMENTS OF THE INVENTION

In the polyorganosiloxane compound according to the invention the functional organic group d) has the preferably formula (VIII):

$$\text{-A-E-A'-} \quad \quad \quad (VIII)$$

wherein E is preferably selected from the groups of the following general formulae $E^5$, $E^6$ and $E^7$:

$$-\{[GLY'\text{-}GLY''\text{-}GLY']\text{-}ACD\}_{q1}\text{-}GLY'_{q2}\text{-}, \quad \quad E^5:$$

$$-\{[GLY'\text{-}GLY''\text{-}GLY''']\text{-}AM\}_{q1}\text{-}GLY'_{q2}\text{-}, \text{ and} \quad \quad E^6:$$

$$-\{[GLY'\text{-}GLY''\text{-}GLY''']\text{-}AM\}_{q1}GLY'''_{q2}\text{-}. \quad \quad E^7:$$

with
q1=0 to 12, preferred 0 to 6, more preferred 0 to 3
q2>0
q1+q2=1 to 24, preferred 1 to 12, more preferred 1 to 6, even more preferred 1 to 3, especially 1 and 3,
GLY'=—CH$_2$CH(OH)CH$_2$O—
GLY''=—R$^4$—O—
GLY'''=—CH$_2$CH(OH)CH$_2$—
ACD=—C(O)—R$^5$—C(O)O—
AM=—N(R$^6$)—R$^5$—N(R$^6$)—
R$^6$ is selected from C1-C22-alkyl, C1-C22-fluoroalkyl or aryl or part of a ring system with R$^5$, preferably C1-C12-alkyl, preferred C1-C6-alkyl, more preferred C1-C3-alkyl, most preferred methyl, C1-C12-fluoroalkyl or aryl or part of a four to eight membered, preferred six membered ring system with R$^5$,
R$^5$ is selected from a bivalent straight chain, cyclic and/or branched C2-C40 hydrocarbon residue which is optionally interrupted by —O—, trivalent N, —NR$^6$—, —C(O)— —C(S)—, and optionally substituted with —OH, or part of a ring system with R$^6$, wherein R$^6$ is defined as above, preferably R$^5$ is a bivalent straight chain, cyclic and/or branched C2-C24, preferred C2-C12, more preferred C2-C6, even more preferred C2-C4 hydrocarbon residue which is optionally interrupted by —O—, trivalent N, —NR$^6$—, —C(O)—, —C(S)—, and optionally substituted with —OH, or part of a ring system with R$^6$, wherein R$^6$ is defined as above, more preferably under the proviso that R$^5$ between two N atoms is at least C2.

Preferred examples for R$^5$ are:
—CH$_2$—, —(CH$_2$)$_2$—, —(CH$_2$)$_4$—, —(CH$_2$)$_6$—, —(CH$_2$)$_8$—, —(CH)$_{10}$—,
—CH$_2$CH(OH)—, —CH(OH)CH(OH)—, —CH(OH)CH(OH)CH(OH)CH(OH)—,
—CH=CH—,
—CH$_2$CH$_2$CH$_2$OCH$_2$CH$_2$CH$_2$—,

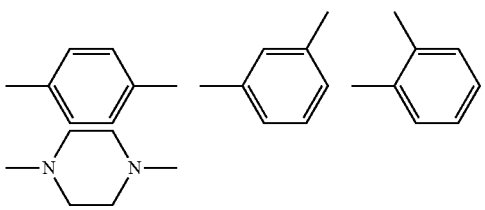

(ring system R⁶+R⁵ with two C atoms between two N atoms).

R⁴ preferably is a bivalent straight chain, cyclic and/or branched and/or aromatic C2-C15, preferred C2-C6 hydrocarbon residue which is optionally interrupted by —O—, —C(O)—, —C(S)—, and optionally substituted with —OH, Preferred examples for R⁴ are:

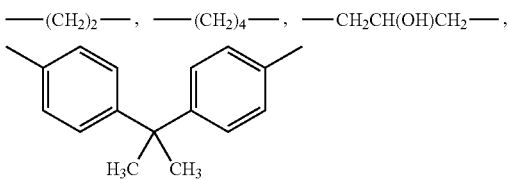

In the polyorganosiloxane structural unit with the general formula S of general formula (X):

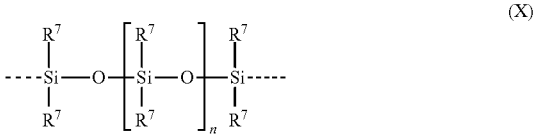

wherein

------ denotes a single bond to K, as defied above,
R⁷ is selected from C1-C22-alkyl, C1-C22-fluoroalkyl or aryl,
n is 0 to 1000, preferred 0 to 500, more preferred 0 to 300, even more preferred 0 to 200, specifically 0 to 100 or in some instances >200 to 1000.
K (in the group —K—S—K— of formula (IX)) is preferably a bivalent or trivalent straight chain, cyclic or branched C2-C20 hydrocarbon residue which is optionally interrupted by —O—, —NH—, trivalent N, —NR¹—, —C(O)—, —C(S)—, and optionally substituted with —OH.

In the polyorganosiloxanes of the invention the positive charges resulting from the ammonium group(s), are neutralized with inorganic anions such as chloride, bromide, hydrogen sulfate, sulfate, or organic anions, like carboxylates deriving from C1-C30 carboxylic acids, for example acetate, propionate, octanoate, especially from C10-C18 carboxylic acids, for example decanoate, dodecanoate, tetradecanoate, hexadecanoate, octadecanoate and oleate, alkylpolythercarboxylate, alkylsulphonate, arylsulphonate, alkylarylsulphonate, alkylsulphate, alkylpolyethersulphate, phosphates derived from phosphoric acid mono alkyl/aryl ester and phosphoric acid dialkyl/aryl ester. The properties of the polyorganosiloxane compounds can be inter alia modified based upon the selection of acids used.

Quaternary ammonium groups as contained in the polyorganosiloxanes of the invention are usually generated by reacting the di-tertiary amines with an alkylating agents, selected from in particular diepoxides (sometimes referred to also as bis-epoxides) in the presence of mono carboxylic acids and difunctional dihalogen alkyl compounds.

R⁷ is more preferred C1-C18 alkyl, C1-C18 fluoroalkyl and aryl. Furthermore, R⁷ is preferably C1-C18 alkyl, C1-C6 fluoroalkyl and aryl. Furthermore, R⁷ is preferably C1-C6 alkyl, C1-C6 fluoroalkyl, more preferably C1-C4 fluoroalkyl, and phenyl. Even more preferably, R⁷ is methyl, ethyl, trifluoropropyl and phenyl.

In the framework of the present invention, the term "C1-C22 alkyl" means in particular that the aliphatic hydrocarbon groups possess from 1 to 22 carbon atoms which can be straight chain or branched. Methyl, ethyl, propyl, n-butyl, pentyl, hexyl, heptyl, nonyl, decyl, undecyl, isopropyl, neopentyl and 1,2,3-trimethyl hexyl serve as examples.

In the framework of the present invention, the concept "C1-C22 fluoroalkyl" means in particular aliphatic hydrocarbon compounds with 1 to 22 carbon atoms which can be straight chain or branched and are substituted with at least one fluorine atom. Monofluormethyl, monofluoroethyl, 1,1,1-trifluorethyl, perfluoroethyl, 1,1,1-trifluoropropyl, 1,2,2-trifluorobutyl are presented as examples.

In the framework of the present invention, "aryl" means in particular unsubstituted or phenyl substituted once or several times with OH, F, Cl, CF3, C1-C6 alkyl, C1-C6 alkoxy, C3-C7 cycloalkyl, C2-C6 alkenyl or phenyl. The expression can also mean naphthyl if need be.

In a preferred embodiment the polyorganosiloxane compounds according to the invention are of the general formulas (Ib) and (Ic):

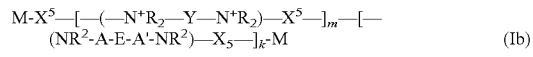 (Ib)

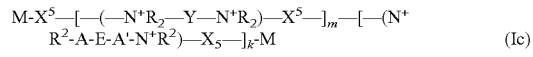 (Ic)

wherein
m is >0, preferred 0.01 to 100, more preferred 0.1 to 100, even more preferred 1 to 100, specifically 1 to 50, more specifically 1 to 20, even more specifically 1 to 10,
k is 0 or an average value of >0 to 50 preferred 1 to 20, more preferred 1 to 10,
M represents a terminal group, comprising terminal ester groups selected from
—OC(O)—Z
—OS(O)₂—Z
—OS(O₂)O—Z
—OP(O)(O—Z)OH
—OP(O)(O—Z)₂
wherein Z is as defined above,
-A-E-A'- is as defined above,
R⁸ is selected from hydrogen or R as defined above,
X⁵ is a group of the formula:

—K—S—K— and -A-E-A'- or -A'-E-A-, each as defined above, and
Y is a as defined above.

In such formulas the repeating units are usually in a statistical arrangement (i.e not a block-wise arrangement).

In a further preferred embodiment the polyorganosiloxane compounds may be also of the general formulas (IIa) or (IIb):

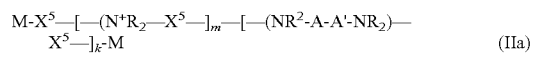 (IIa)

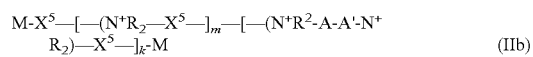 (IIb)

wherein each group is as defined above. Also in such formula the repeating units are usually in a statistical arrangement (i.e not a block-wise arrangement).

Z in the groups M:
—OC(O)—Z
—OS(O)$_2$—Z
—OS(O$_2$)—Z
—OP(O)(O—Z)OH
—OP(O)(O—Z)$_2$
is preferably is a straight chain, cyclic or branched saturated or unsaturated C1-C20, preferred C2 to C18, even more preferred-hydrocarbon radical, which can be interrupted by one or more —O—, or —C(O)— and substituted with —OH.

Preferred groups terminal groups M are —OC(O)—Z resulting from carboxylic acids in particular with more than 10 carbon atoms like for example dodecanoic acid.

In a preferred embodiment of the invention the molar ratio of the polyorganosiloxane-containing repeating group —K—S—K— and the repeating group -A-E-A'- or -A'-E-A- is between 100:1 and 1:100, preferred between 20:1 and 1:20, even more preferred between 10:1 and 1:10.

In the group —(N$^+$R$_2$—Y—N$^+$R$_2$)— the groups R preferably represent a monovalent straight chain, cyclic or branched C1-C20 hydrocarbon radical, which can be interrupted by one or more —O—, —C(O)— and can be substituted by —OH, Y is preferably represent a divalent straight-chain, cyclic, or branched C1-C20 hydrocarbon radical, which can be interrupted by —O—, —C(O)— and can be substituted by hydroxyl.

The viscosities of the neat polysiloxane polymers according to the invention preferably are 500 to 100000 mPa·s, preferred 500 to 70000 mPa·s, more preferred 500 to 50000 mPa·s, even more preferred 500 to 20000 mPa·s, specifically 500 to 10000 mPa·s, more specifically 500 to 5.000 mPa·s determined at 20° C. (Brookfield, spindle 4, 12 RPM). The molecular weight is between 10,000 and 100,000 g/mol measured as weight average Mw per GPC (gel permeation chromatography) and polystyrene as standard.

The molar ratio of the polyorganosiloxane-containing repeating group —K—S—K— and the hydroxylated ester and/or ether and/or amino group -A-E-A'- or -A'-E-A- can be controlled as shown below via the selection of the molar ratio of the parent compounds, especially the ratio of the α,ω-halogen alkyl carboxylic acid ester or epoxy compounds preferably used in the invention and the polyorganosiloxane-bis epoxide compounds. The properties of the products depend essentially upon the ratio of the parent materials used, and upon the length of the functional organic group (d), comprising one or more hydroxyl groups and at least one functional group selected from an ester group, an ether group and an amino group, (sometimes referred to as hydroxylated ester and/or ether and/or amino group) or polyorganosiloxane blocks contained therein.

In a preferred embodiment of the invention, K is a divalent hydrocarbon radical having at least 4 carbon atoms, which contains one hydroxy group and can be interrupted by one oxygen atom. Such groups include for example:

—(CH$_2$)$_3$OCH$_3$CHCH$_2$—        —(CH$_2$)$_3$OCH$_2$CH—
         |                                               |
         OH                                          CH$_2$OH

—(CH$_2$)$_2$—⌬—OH

-continued

—(CH$_2$)$_2$—⌬—OH

—CH$_2$CH—⌬—OH, CH$_3$
     |
     CH$_3$

—CH$_2$CH—⌬—CH$_3$, OH
     |
     CH$_3$

In the groups
—(NR$^2$-A-E-A'-NR$^2$)— and —(N$^+$R$^2_2$-A-E-A'-N$^+$R$^2_2$)—
preferably, the group -A-E-A'- is represented by a group of the formula -A-{[GLY'-GLY''-GLY']-ACD}$_{q1}$-GLY'$_{q2}$-A'-, -A-{[GLY'-GLY''-GLY''']-AM}$_{q1}$-GLY'$_{q2}$-A'-, and A-{[GLY'-GLY''-GLY''']-AM}$_{q1}$GLY'''$_{q2}$-A'-, wherein the indices are preferably:
q1=0 to 12, preferred 0 to 6, more preferred 0 to 3
q2>0
q1+q2=1 to 24, preferred 1 to 12, more preferred 1 to 6, even more preferred 1 to 3, especially 1 and 3,
and in
GLY'=—CH$_2$CH(OH)CH$_2$O—
GLY''=—R$^4$—O—
GLY'''=—CH$_2$CH(OH)CH$_2$—
ACD=—C(O)—R$^5$—C(O)O—
AM=—N(R$^6$)—R$^5$—N(R$^6$)—
the indices are preferably
R$^6$=C1-C22-alkyl, C1-C22-fluoroalkyl or aryl or part of a ring system with R$^5$
R$^5$=bivalent straight chain, cyclic and/or branched C2-C40 hydrocarbon residue which is optionally interrupted by —O—, trivalent N, —NR$^6$—, —C(O)—, —C(S)—, and optionally substituted with —OH, or part of a ring system with R$^6$, wherein R$^6$ is defined as above,
R$^4$=a bivalent straight chain, cyclic and/or branched and/or aromatic C2-C40 hydrocarbon residue which is optionally interrupted by —O—, —C(O)—, —C(S)—, and optionally substituted with —OH, and
with A and A' as defined above.

In a preferred embodiment is
R$^7$=C1-C12-alkyl, preferred C1-C6-alkyl, more preferred C1-C3-alkyl, most preferred methyl,
R$^5$=a bivalent straight chain, cyclic and/or branched C2-C24, preferred C2-C12, more preferred C2-C6, even more preferred C2-C4 hydrocarbon residue which is optionally interrupted by —O—, trivalent N, —NR$^6$—, —C(O)—, —C(S)—, and optionally substituted with —OH, or part of a ring system with R$^6$, wherein R$^6$ is defined as above, under the proviso that R$^6$ between two N atoms is at least C2.
Preferred examples for R$^6$ are
—CH$_2$—, —(CH$_2$)$_2$—, —(CH$_2$)$_4$—, —(CH$_2$)$_6$—, —(CH$_2$)$_8$—, —(CH$_2$)$_{10}$—,
—CH$_2$CH(OH)—, —CH(OH)CH(OH)—, —CH(OH)CH(OH)CH(OH)—,
—CH=CH—,
—CH$_2$CH$_2$CH$_2$OCH$_2$CH$_2$CH$_2$—,

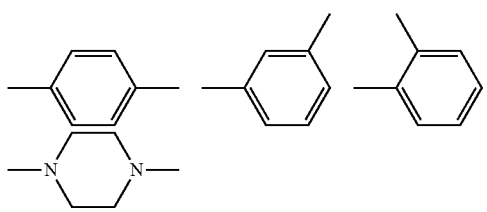

ring system $R^6+R^5$ with two C atoms between two N atoms) and for $R^4$=a bivalent straight chain, cyclic and/or branched and/or aromatic C2-C15, preferred C2-C6 hydrocarbon residue which is optionally interrupted by —O—, —C(O)—, —C(S)—, and optionally substituted with —OH, Preferred examples for $R^4$ are

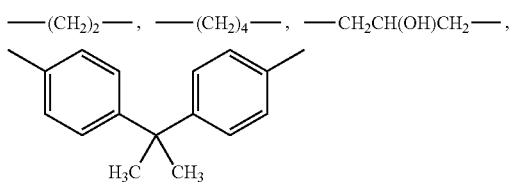

The polyorganosiloxane compounds of the invention are preferentially produced in a first embodiment via a method, in which first α,ω Si—H functionalized siloxanes of the general structure

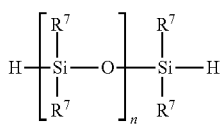

wherein $R^7$ and n are as defined above, and R7 is preferred methyl, are converted, in the presence of a hydrosilylation catalyst and at temperatures of 50° to 150° C., with 1.0 to 1.5 mol, based upon SiH groups, of an alkenyl-epoxide, which has a terminal olefinic bond, wherein the alkenyl-epoxide contains at least 4 carbon atoms, and may additionally contain a non-cyclical ether group. Vinyl cyclohexene oxide and allyl glycidyl ether are preferably used as epoxy-functional precursors for the production of epoxy functionalized siloxanes. The excess olefinic epoxide is then removed, if necessary. The bisepoxide is preferably reacted with a mixture of one diamine, for example the preferred diamine of the formula

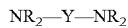

with R and T as defined above, and preferably one α,ω epoxy compound, α,ω halogen alkyl ether compound or α,ω carboxylic halogen alkyl acid ester, preferably of the formula L-A-E-A'-L or L-A-E-A'-L wherein A-E-A' or A'-E-A are as defined above and X is a customary nucleophilic leaving group, preferably chloride or bromide, provided that L is bonded to a terminal —CH2- group, in the presence of an organic acid at preferred 40° to 150° C., wherein the molar ratio of tertiary amino groups: carboxylic haloacid ester/haloalkyl ether groups is for example ≥1:1, the molar ratio of tertiary amino groups:Σ (epoxy groups+carboxylic haloacid ester/haloalkyl ether groups) is for example ≤1:1, preferred ≤0.98:1, more preferred ≤0.9:1, even more preferred ≤0.7:1, specifically ≤0.5:1, the molar ratio of organic acid:epoxy groups ranges from 3:1 to 1:1, preferred from 2:1 to 1:1, more preferred from 1.5:1 to 1:1, even more preferred from 1.2:1 to 1:1, specifically is 1:1.

This means that i.e. either by reduction of the molar amount on tertiary amine and/or increase of the molar amount of organic acids low viscosity polyorganosiloxane compounds of the invention can be synthesized.

In a preferred variation of the embodiment, the species that contain the various amino groups may be added to the batch together with the carboxylic haloacid ester or haloalkyl ether derivatives, if necessary with the simultaneous addition of equimolar quantities of acid. It is also within the scope of the invention, however, to cause first the epoxy derivatives, the carboxylic haloacid ester derivatives or haloalkyl ether derivatives, and the di-tertiary amines to react in the presence of a quantity of acid that is equivalent to that of the epoxy groups, and then, if necessary, to add additional GLY and GLY' containing monomers that contain primary or secondary amino groups, if necessary with the addition of acids to the point of equivalence with the amino groups.

It is likewise possible to bring the carboxylic haloacid ester or haloalkyl ether derivatives and the di-tertiary amines to react, forming hydrophilic blocks, and afterwards to add the epoxy derivatives, if necessary adding GLY and GLY' derivatives that contain primary or secondary amino groups, in the presence of a quantity of acid that is equivalent to that of the epoxy groups to the reaction mixture.

It is preferred to use bis-carboxylic haloacid esters or bis-haloalkyl ethers of glycerol or oligoglycerols, such alpha,omega-bis-chloroacetic estera or alpha,omega-bis-chlorocthyl ethers of glycerol or oligoglycerols, alpha, omega-bis-amino terminated glycerol or oligoglycerols, alpha,omega-bis-epoxy terminated glycerol or oligoglycerols as precursors for the glycerol or oligoglycerol moiety in the siloxane copolymers.

During the time in which the individual components mare being added, the sequential distribution in the polymers being formed can be influenced.

It is further within the scope of the invention to cause several siloxane components and/or GLY and GLY' derivatives of various chain lengths to react, while maintaining the desired overall stoichiometry. From this, there follows, e.g., the possibility of creating a desired siloxane chain length by using a single siloxane component or by the purposeful mixture of several siloxane components. Analogously, it is possible to prepare an advantageous average GLY and GLY' block length in the form of a monomodal, bimodal, or polymodal dispersion. Further, a desired share of GLY and GLY' monomers can be distributed variably between the carboxylic haloacid ester or haloalkyl ether components and the amino components.

Parent materials for the production of the preferred α,ω carboxylic haloacid esters, preferably of the formula

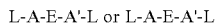

wherein L is preferably chlorine, bromine, are glycerol, diglycidyl ether, glycerol diglycidyl ether, 1,4-butylenglycol diglycidyl ether and bisphenol A diglycidyl ether. The esterification of the OH groups is accomplished via known methods. For descriptions of said methods please refer to U.S. Pat. No. 7,217,777, example 11a. The esterification of epoxy functional glycerol derivatives is also accomplished via known methods. For descriptions of said methods please refer to US 2012/0289649, example 1 and U.S. Pat. No. 2,780,642.

Parent materials for the production of the preferred α,ω-haloalkyl ethers, preferably of the formula

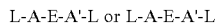

wherein L is preferably chlorine, are diglycidyl ether, glycerol diglycidyl ether, 1,4-butylenglycol diglycidyl ether and bisphraol A diglycidyl ether. The etherification of epoxy functional derivatives with alcohols is accomplished in the presence of an acid catalyst (US 2012/0035386).

Parent materials for the production of the preferred α,ω-amino terminated structures, preferably of the formula

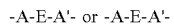

are diglycidyl ether, glycerol diglycidyl ether, 1.4.-butylenglycol diglycidyl ether and bisphenol A diglycidyl ether. The epoxy ring opening of epoxy functional glycerol derivatives with amines is also accomplished via known methods. For descriptions of said methods please refer to US 2009/0076238, example 3.

The quaternization and alkylation reactions are preferably run in polar organic solvents.

Suitable solvents are, for example organic solvents and water, including in particular mixtures of organic solvents and water, preferably polar organic solvents and water. Polar organic solvents include generally those comprising at least one heteroatome, like in particular oxygen, e.g., alcohols, especially methanol, ethanol, i-propanol and n-butanol; glycols, such as ethylene glycol, diethylene glycol, triethylene glycol, their methyl-, ethyl- and butyl others, 1,2-propylene glycol, dipropylene glycol, tripropylene glycol, their methyl-, ethyl- and butyl ethers and 1,3-propylene glycol; ketones, such as acetone and methylethylketone; esters, such as ethylacetate, butylacetate, methoxypropylacetate and 2-ethyl-hexylacetate; others, such a tetrahydrofuran; and nitro compounds, such as nitromethane.

It is preferred to run the reactions with a weight ratio of Σ polymer components:Σ(organic solvents+water) in a weight-range from 100:0 to 20:80, preferably 99.999:0.001 to 20:80, more preferred 95:5 to 20:80, still more preferred 95:5 to 50:50, even more preferred 95:5 to 60:40.

The amount on water in the composition of the reaction ranges in one embodiment from 0.1-0.5 wt. % wt. %, in another one preferably from 0.01-0.1; in another embodiment the amount is in the range of 2-10 wt. % and preferably between 0.5-2 wt. %. In a preferred embodiment of the invention the desired amount on water is added separately. It is also possible to add the desired amount on water i.e. in form of solvent azeotropes or by the amount which is present in commercial grades.

The above described polyorganosiloxane compounds comprising quaternary ammonium functions and ester functions may contain individual molecules which contain quaternary ammonium functions and no ester functions, molecules which contain quaternary ammonium functions and ester functions as well as molecules which contain ester functions and no quaternary ammonium functions.

The above described polyorganosiloxane compounds comprising quaternary ammonium functions and ester functions are to be understood as mixtures of molecules comprising a certain averaged amount and ratio of both moieties.

Another embodiment of the invention relates to polyorganosiloxane compositions, comprising:
A) a polyorganosiloxane compound comprising:
  at least one polyorganosiloxane group (a),
  at least one quaternary ammonium group (b),
  at least one terminal ester group (c),
  at least one functional organic group (d), comprising one or more hydroxyl groups and
at least one functional group selected from an ester group, an ether group and an amino group, and
B) at least one polyorganosiloxane compound, comprising at least one terminal ester group, which polyorganosiloxane compound is different from polyorganosiloxane compound A).

Such polyorganosiloxane compositions comprising quaternary ammonium functions and polyorganosiloxane compounds comprising ester functions are physically mixed in order to adjust the desired quat (N$^+$): ester ratio and the desired viscosity according to the invention. Both compounds are mixed in a ratio which fulfils the above outlined viscosity requirement according to the invention. The mixtures have a viscosities at 20° C. and a shear rate of 0.1 s<−1> of <100000 mPas, preferred <50000 mPas, even more preferred <20000 mPas, specifically <10000 mPa·s, more specifically <5000 mPa·s. The polyorganosiloxane compounds A) comprising quaternary ammonium functions are i.e. known from U.S. Pat. No. 7,217,777. The synthesis of polyorganosiloxane compounds comprising ester functions is known from US2012/0289649. They can i.e. be synthesized from the corresponding epoxy siloxanes by esterification with acids in the presence of a tertiary amino catalyst. The preferred polyorganosiloxane compounds B) comprising ester functions are α,ω-ester modified derivatives of the structure M-(K—S—K)-M (wherein M, K, and S are as defined above) having siloxane chain length in range from n=0 to 1000, preferred 0 to 500, more preferred 0 to 300, even more preferred 0 to 200, specifically 0 to 100. Alternatively, comb-like derivatives comprising ester function as side groups in a difiunctional siloxane unit (OSiMeR* with R*=carbon bound ester group)), and optionally terminal ester moieties (O$_{1/2}$SiMe$_2$R* with R*=carbon bound ester group) of the same chain length range of n are also preferred. The number of ester-group-containing siloxy units is preferably from 1 to 500, preferred 1 to 250, more preferred 1 to 150, even more preferred 1 to 100, specifically 1 to 50, even more specific 1 to 25.

Preferred monofunctional organic acids yielding the esters are the ones forming the above mentioned counter ions. Preferred examples are C1-C30 carboxylic acids, for example C2, C3, C8 acids, C10-C18 carboxylic acids, for example C12, C14, C16 acids, saturated, unsaturated and hydroxyl functionalized C18 acids, alkylpolythercarboxylic acids, alkylsulphonic acids, arylsulphonic acids, alkylarylsulphonic acids, alkylsulphric acids, alkylpolyetheraulphuric acids, phosphoric acid mono alkyl/aryl esters and phosphoric acid dialkyl/aryl esters.

The invention further relates to the use of the above-described polyorganosiloxane compounds in cosmetic formulations for skin and hair care, in polishing agents for treating and coating hard surfaces, in formulations for drying automobiles and other hard surfaces, for example following automatic washing, for finishing textiles and textile fibers, as separate softeners for use after textiles have been washed with non-ionogenic or anionic/non-ionogenic detergent formulations, as softeners in formulations for washing textiles that are based upon non-ionic or anionic/non-ionic surfactants, and as means for preventing or removing wrinkles in textiles.

The invention further relates to the use of the above-described polyorganosiloxane compounds as wash-resistant, hydrophilic softeners for use in the original finishing of textiles.

The invention further relates to compositions that contain at least one of the polyorganosiloxane compounds, together with at least one additional component that is commonly used in such a composition Below, a number of typical examples of these types of compositions are provided, in which the polyorganosiloxane compounds of the invention may be advantageously used:

Typical adjuvants in these types of compositions are, e.g., those materials described in A. Domsch: Die kosmetischen Pracparatc [Cosmctic Preparations] Vol. I and II, 4th Edition, Verl. fuer chem. Industrie [Publishers for the Chemical Industry], U. Ziolkowsky K G, Augsburg, and the International Cosmetic Ingredient Dictionary and Handbook 7th Ed. 1997 by J. A. Wenninger, G. N. McEwen Vol. 1-4 by The Cosmetic, Toiletry and Fragrance Association Washington D.C.

Anionic Shampoo

This formulation example is intended as a basic formulation. Anionic shampoos customarily contain, but are not limited to, the following components:

Alkylsulfates, alkylether sulfates, sodium lauryl sulfate, sodium lauryl ether sulfate, ammonium lauryl sulfate, ammonium lauryl-ether sulfate, TEA-lauryl sulfate, TEA-lauryl-ether sulfate, alkylbenzene sulfonates, α-olefinsulfonates, paraffin sulfonates, sulfosuccinates, N-acyltaurides, sulfate-glycerides, sulfatized alkanolamides, carboxylate salts, N-acyl-amino acid salts, silicones, etc.

| Components | wt-% |
|---|---|
| Ammonium lauryl sulphate 10.00-30.00 | 10.00-30.00 |
| Ammonium lauryl-ether sulphate | 5.00-20.00 |
| Cocamidopropyl betaine | 0.00-15.00 |
| Lauramide DEA | 0.00-5.00 |
| Cocamide Mea | 0.00-5.00 |
| Dimethicone copolyol (dimethylsiloxane glycol copolymer) | 0.00-5.00 |
| Cyclopentasiloxane | 0.00-5.00 |
| Polyorganosiloxane compound of the invention | 0.50-5.00 |
| Polyquaternium-10 | 0.00-2.00 |
| Preservatives | 0.00-0.50 |
| Fragrance | 0.00-5.00 |
| Deionized water | q.s. 100% |
| Sodium chloride | q.s. |

Non-Ionic Shampoo

This formulation example is intended as a basic formulation. Non-ionic shampoos customarily contain, but are not limited to, the following components:

Monoalkanolamides, monoethanolamides, monoisopropanolamides, polyhydroxy derivatives, sucrose monolaurate, polyglycerine ether, amine oxides, polyethoxylated derivatives, sorbitol derivatives, silicones, etc.

| Components | wt-% |
|---|---|
| Lauramide DEA | 10.00-30.00 |
| Lauramide oxide | 5.00-20.00 |
| Cocamide Mea | 0.00-5.00 |
| Dimethicone copolyol | 0.00-5.00 |

| Components | wt-% |
|---|---|
| Polyorganosiloxane compound of the invention | 0.50-5.00 |
| Preservatives | 0.00-0.50 |
| Fragrance | 0.00-5.00 |
| Deionized water | q.s. 100% |
| Sodium chloride | q.s. |

Amphoteric Shampoo

This formulation example is intended as a basic formulation. Formulations of this category customarily contain, but are not limited to, the following components: N-alkyl-iminodipmpionates, N-alkyl-iminopropionates, amino acids, amino acid derivatives, amido betaine, imidazolinium derivatives, sulfobetaines, sultaines, betaines, silicones, etc.

| Components | wt-% |
|---|---|
| PEG-80-sorbitane laurate | 10.00-30.00 |
| Lauroamphoglycinate | 0.00-10.00 |
| Cocamidopropyl-hydroxysultain | 0.00-15.00 |
| PEG-150-distearate | 0.00-5.00 |
| Laurylether-13-carboxylate | 0.00-5.00 |
| Polyorganosiloxane compound of the invention | 0.50-5.00 |
| Fragrance | 0.00-5.00 |
| Deionized water | q.s. 100% |
| Sodium chloride | q.s. |

Cationic Shampoo

This formulation example is intended only as a basic formulation. Formulations of this category customarily contain, but are not limited to, the following components:

Bis-quaternary ammonium compounds, bis-(trialkylammonium acetyl)diamines, amido amines, ammonium alkylesters, silicones, etc.

| Components | wt-% |
|---|---|
| Laurylether-13-carboxylate | 10.00-30.00 |
| Isopropylmyristate | 5.00-20.00 |
| Cocamidopropyl-betaine | 0.00-15.00 |
| Lauramide DEA | 0.00-5.00 |
| Cocamide MEA | 0.00-5.00 |
| Polyorganosiloxane compound of the invention | 0.50-5.00 |
| Preservatives | 0.00-0.50 |
| Fragrance | 0.00-5.00 |
| Deionized water | q.s. 100% |
| Sodium chloride | q.s. |

Setting Agents

This formulation example is intended only as a basic formulation. Formulations of this category customarily contain, but are not limited to, the following components:

Fatty acids, fatty acid esters, ethoxylated fatty acids, ethoxylated fatty acid esters, fatty alcohols, ethoxylated fatty alcohols, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickeners, silicones, etc.

| Components | wt-% |
| --- | --- |
| Ceteareth-20 | 0.10-10.00 |
| Steareth-20 | 0.10-10.00 |
| Stearyl alcohol | 0.10-10.00 |
| Stearamidopropyl-dimethylamine | 0.00-10.00 |
| Dicetyldimonium-chloride | 0.00-10.00 |
| Polyorganosiloxane compound of the invention | 0.50-5.00 |
| Cyclopentasiloxane | 0.00-5.00 |
| Dimethicone | 0.00-5.00 |
| Preservatives | 0.00-0.50 |
| Fragrance | 0.00-5.00 |
| Deionized water | q.s. 100% |

"Clear Rinse-Off" Setting Agents

This formulation example is intended as a basic formulation. Formulations of this category customarily contain, but are not limited to, the following components:
Fatty acids, fatty acid esters, ethoxylated fatty acids, ethoxylated fatty acid esters, fatty alcohols, ethoxylated fatty alcohols, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickening agents, silicones, etc.

| Components | wt-% |
| --- | --- |
| Glycerin | 0.10-10.00 |
| Cetrimonium chloride | 0.00-10.00 |
| Polyorganosiloxane compound of the invention | 0.50-5.00 |
| Hydroxyethyl cellulose 0.00-5.00 | 0.00-5.00 |
| Preservatives | 0.00-0.50 |
| Fragrance | 0.00-5.00 |
| Deionized water | q.s. 100% |

Foam Setting Agents for Hair

This formulation example is intended as a basic formulation. Formulations of this category contain, but are not limited to, the following components:
Fatty acids, fatty acid esters, ethoxylated fatty acids, ethoxylated fatty acid esters, fatty alcohols, ethoxylated fatty alcohols, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants thickening agents, silicones, solvents, ethanol, isopropanol, isoparaffin solvents, butane, propane, isobutane, CFC's fluorated aerosol propellants, dimethylether, compressed gases, etc.

| Components | wt-% |
| --- | --- |
| Polyorganosiloxane compound of the invention | 0.50-5.00 |
| Nonoxynol-15 | 0.00-2.00 |
| Nonoxynol-20 | 0.00-2.00 |
| Aerosol propellants | 0.00-20.00 |
| Preservatives | 0.00-0.50 |
| Fragrance | 0.00-5.00 |
| Deionized water | q.s. 100% |

Pump Spray (Setting Agents) for Hair

This formulation example is intended only as a basic formulation. Formulations of this category customarily contain, but are not limited to, the following components:
Fatty acids, fatty acid esters, ethoxylated fatty acids, ethoxylated fatty acid esters, fatty alcohols, ethoxylated fatty alcohols, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickening agents, silicones, solvents, ethanol, isopropanol, isoparrafin solvents, etc.

| Components | wt-% |
| --- | --- |
| Polyorganosiloxane compound of the invention | 0.50-5.00 |
| Cyclomethicone | 0.00-80.00 |
| Ethanol | 0.00-80.00 |
| Preservatives | 0.00-0.50 |
| Fragrance | 0.00-5.00 |
| Deionized water | q.s. 100% |

Setting Agent Spray for Hair

This formulation example is intended as a basic formulation. Formulations of this category customarily contain, but are not limited to, the following components:
Fatty acids, fatty acid esters, ethoxylated fatty acids, ethoxylated fatty acid eaters, fatty alcohols, ethoxylated fatty alcohols, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickening agents, silicones, solvents, ethanol, isopropanol, isoparaffin solvents, butane, propane, isobutane, CFC's fluorated aerosol propellants, dimethylether, compressed gases, etc.

| Components | wt-% |
| --- | --- |
| Polyorganosiloxane compound of the invention | 0.50-5.00 |
| Cyclomethicone | 0.00-80.00 |
| Ethanol | 0.00-50.00 |
| Aerosol propellants 0.00-50.00 | 0.00-50.00 |
| Preservatives | 0.00-0.50 |
| Fragrance | 0.00-5.00 |
| Deionized water | q.s. 100% |

Gel Setting Agents for Hair

This formulation example is intended as a basic formulation. Formulations of this category customarily contain, but are not limited to, the following components: thickening agents, cellulose derivatives, acrylic acid derivatives, fixative polymers, conditioning chemicals, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, silicones, solvents, ethanol, isopropanol, isoparaffin solvents, etc.

| Components | wt-% |
| --- | --- |
| Polyorganosiloxane compound of the invention | 0.50-5.00 |
| Hydroxyethyl cellulose | 0.00-2.00 |
| Citric acid | 0.00-2.00 |
| Preservatives | 0.00-0.50 |
| Fragrance | 0.00-5.00 |
| Deionized water | q.s. 100% |

Rinse Off Conditioner

This formulation example is intended as a basic formulation. Formulations of this category customarily contain, but are not limited to, the following components: hydrocarbon based cationic conditioning agents, silicone based cationic conditioning agents, high melting fatty compounds, low melting oil like ester compounds, thickening agents, cellulose derivatives, fixative polymers, ethylene glycols, propylene glycols, glycol ester, glycerin, glycerin esters, monohydric alcohols, polyhydric alcohols, cationic polymers, nonionic and betain co-emulsifiers, silicones, complexing agents, solvents, fragrances, vitamins, solvents, etc.

| Components | wt-% |
| --- | --- |
| Polyorganosiloxane compound of the invention | 0.50-5.00 |
| Cetyl Hydroxyethyl cellulose | 0.00-3.00 |
| Cetearyl alcohol 0.00-3.00Citric acid | 0.00-2.00 |
| Glyceryl stearate and PEG-100 Stearate | 0.00-3.00 |
| Tetrasodium EDTA | 0.00-1.00 |
| Deionized water | q.s. 100% |

Styling Gel for Hair

This formulation example is intended as a basic formulation. Formulations of this category customarily contain, but are not limited to, the following components:
Fixative polymers, lacquers, acrylic acid derivatives, cellulose derivatives, vinyl derivatives, conditioning chemicals, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickening agents, silicones, solvents, ethanol, isopropanol, isoparaffin solvents, etc.

| Components | wt-% |
| --- | --- |
| Polyorganosiloxane compound of the invention | 0.50-5.00 |
| Fixing agents | 0.10-10.00 |
| Hydroxyethyl cellulose | 0.00-2.00 |
| Citric acid | 0.00-2.00 |
| Fragrance | 0.00-5.00 |
| Deionized water | q.s. 100% |

Styling Spray for Hair

This formulation example is intended as a basic formulation. Formulations of this category customarily contain, but are not limited to, the following components:
Fixative polymers, lacquers, vinyl derivatives, fatty acids, fatty acid esters, ethoxylated fatty acids, ethoxylated fatty acid esters, fatty alcohols, ethoxylated fatty alcohols, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickening agents, silicones, solvents, ethanol, isopropanol, isoparaffin solvents, butane, propane, isobutane, CFC's fluorated aerosol propellants, dimethylether, compressed gases, etc.

| Components | wt-% |
| --- | --- |
| Polyorganosiloxane compound of the invention | 0.50-5.00 |
| Cyclomethicone 0.00-80.00 | 0.00-80.00 |
| Fixing agents | 0.10-10.00 |
| Ethanol | 0.00-50.00 |
| Aerosol propellants | 0.00-50.00 |
| Preservatives | 0.00-0.50 |
| Fragrance | 0.00-5.00 |
| Deionized water | q.s. 1.00% |

Pump Spray (Styling) for Hair

This formulation example is intended as a basic formulation. Formulations of this category customarily contain, but are not limited to, the following components:
Vinyl derivatives, fixative polymers, lacquers, fatty acids, fatty acid esters, ethoxylated fatty acids, ethoxylated fatty acid esters, fatty alcohols, ethoxylated fatty alcohols, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickening agents, silicones, solvents, ethanol, isopropanol, isoparaffin solvents, butane, propane, isobutane, CFCs fluorated aerosol propellants, dimethylether, compressed gases, etc.

| Components | wt-% |
| --- | --- |
| Polyorganosiloxane compound of the invention | 0.50-5.00 |
| Cyclomethicone 0.00-80.00 | 0.00-80.00 |
| Fixing agents | 0.10-10.00 |
| Ethanol | 0.00-50.00 |
| Preservatives | 0.00-0.50 |
| Fragrance | 0.00-5.00 |
| Deionized water | q.s. 100% |

The use of the polyorganosiloxane derivatives specified in the invention for applications in the hair care field produces favorable results with respect to strengthening shine, fixing (hold), body, volume, moisture regulation, color retention, protection against environmental factors (UV, salt water, etc.), manageability, antistatic properties, ability to dye, etc.

EXAMPLES

The following examples are intended to describe the present invention in greater detail, without limiting its scope.

Example 1

Non-Inventive Polyorganosiloxane

In a 500 ml three necked flask, equipped with refluxing condenser, thermometer and mechanical stirrer, 150 g (58.7 mmol epoxy groups) of a silicone diepoxide of the structure

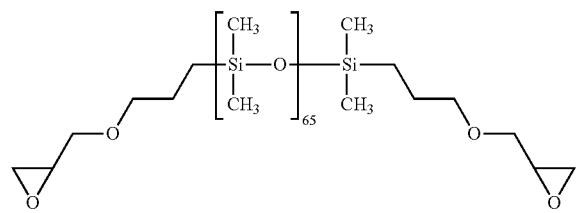

-continued
1.50 g (7 mmol CH$_2$Cl) ClCH$_2$C(O)O[CH$_2$CH(OH)CH$_2$O]$_3$C(O)CH$_2$Cl

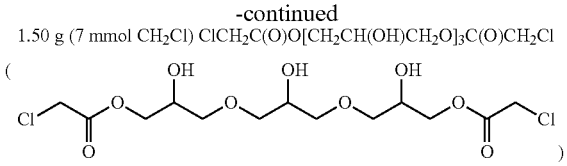

(synthesized from glycerol diglycidyl ether and chloro acetic acid in propylene glycol monomethyl ether, 90% active), 12.56 g (62.8 mmol) lauric acid, 6.06 g N,N,N',N'-tetramethylhexanediamine (70.3 mmol tert. amine), 31.8 g 2-propanol and 10.7 g distilled water are mixed at room temperature. The mixture is heated to reflux for 13.5 hours. Afterwards, the solvents are removed and the material analyzed by means of NMR and viscosimetry (see tab. 1). The molar ratio of the quaternary ammonium groups (b) and the terminal ester groups (c) is 100:12, i.e. outside the claimed range of the molar ratio of less than 100:15.

Example 2

Inventive Polyorganosiloxane
In a 500 ml three-necked flask, equipped with refluxing condenser, thermometer and mechanical stirrer, 150 g (58.7 mmol epoxy groups) of a silicone diepoxide of the structure

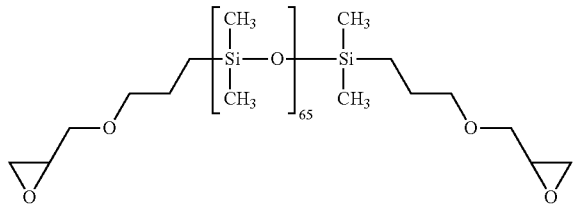

1.50 g (7 mmol CH$_2$Cl) ClCH$_2$C(O)O[CH$_2$CH(OH)CH$_2$O]$_3$C(O)CH$_2$Cl (synthesized from glycerol diglycidyl ether and chloro acetic acid in propylene glycol monomethyl ether, 90% active), 12.56 g (62.8 mmol) lauric acid, 4.54 g N,N,N',N'-tetramethylhexanediamine (52.8 mmol tert. amine), 31.5 g 2-propanol and 10.5 g distilled water are mixed at room temperature. The mixture is heated to reflux for 13.5 hours. Afterwards, the solvents are removed and the material analyzed by means of NMR and viscosimetry (see tab. 1). The molar ratio of the quaternary ammonium groups (b) and the terminal ester groups (c) is 100:28.

Example 3

Inventive Polyorganosiloxane
In a 500 ml three-necked flask, equipped with refluxing condenser, thermometer and mechanical stirrer, 150 g (58.7 mmol epoxy groups) of a silicone diepoxide of the structure

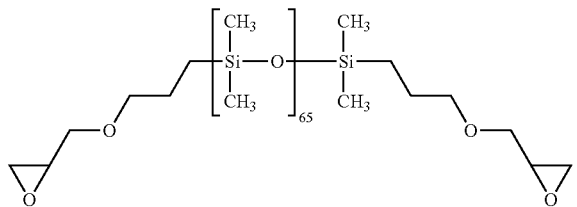

1.50 g (7 mmol CH$_2$Cl) ClCH$_2$C(O)O[CH$_2$CH(OH)CH$_2$O]$_3$C(O)CH$_2$Cl (synthesized from glycerol diglycidyl ether and chloro acetic acid in propylene glycol monomethyl ether, 90% active), 12.56 g (62.8 mmol) lauric acid, 3.03 g N,N,N'N'-tetramethylhexanediamine (35.2 mmol tert. amino groups), 31.2 g 2-propanol and 10.4 g distilled water are mixed at room temperature. The mixture is heated to reflux for 13.5 hours. Afterwards, the solvents are removed and the material analyzed by means of NMR and viscosimetry (see tab. 1). The molar ratio of the quaternary ammonium groups (b) and the terminal ester groups (c) is 100:44.

Example 4

Inventive Polyorganosiloxane
In a 500 ml three-necked flask, equipped with refluxing condenser, thermometer and mechanical stirrer, 150 g (58.7 mmol epoxy groups) of a silicone diepoxide of the structure

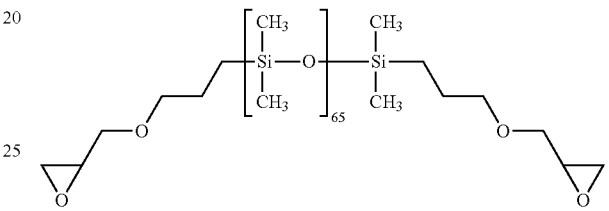

1.50 g (7 mmol CH$_2$Cl) ClCH$_2$C(O)O[CH$_2$CH(OH)CH$_2$O]$_3$C(O)CH$_2$Cl (synthesized from glycerol diglycidyl ether and chloro acetic acid in propylene glycol monomethyl ether, 90% active), 12.56 g (62.8 mmol) lauric acid, 1.51 g N,N,N',N'-tetramethylhexanediamine (17.6 mmol tert. amino groups), 30.9 g 2-propanol and 10.3 g distilled water are mixed at room temperature. The mixture is heated to reflux for 13.5 hours. Afterwards, the solvents are removed and the material analyzed by means of NMR and viscosimetry (see tab. 1). The molar ratio of the quaternary ammonium groups (b) and the terminal ester groups (c) is 100:56.

Example 5

Inventive Polyorganosiloxane
In a 500 ml three-necked flask, equipped with refluxing condenser, thermometer and mechanical stirrer, 0.66 g (7 mmol COOH) chloro acetic acid, 1.43 g (14 mmol epoxy groups) glycidol diglycidyl ether and 0.52 g (7 mmol COOH) tartaric acid are dissolved in 31.2 g 2-propanol. The mixture is heated to reflux for 8 hours. Conversion epoxy groups 100% ($^1$H-NMR).
An ester of the averaged structure

was formed. 150 g (58.7 mmol epoxy groups) of a silicone diepoxide of the structure

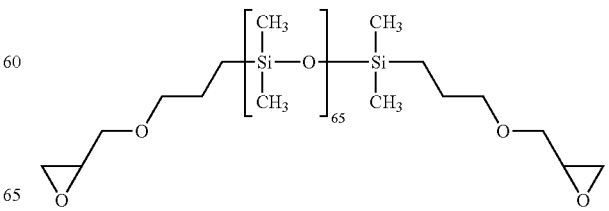

12.56 g (62.8 mmol) lauric acid, 3.03 g N,N,N',N'-tetramethylhexanediamine (35.2 mmol tert. amino groups), 31.2 g 2-propanol and 10.4 g distilled water are mixed at room temperature. The mixture is heated to reflux for 13.5 hours. Afterwards, the solvents are removed and the material analyzed by means of NMR and viscosimetry (see tab. 1). The molar ratio of the quaternary ammonium groups (b) and the terminal ester groups (c) is 100:52.

TABLE 1

| Example # | Solids 120° C./ 30 min | Viscosity mPas 20° C., spindle 4, 12 RPM | Ratio N+:ester** | Dispersibility in water* |
|---|---|---|---|---|
| 1 | 98.14 | 121.000 | 100:12 | very poor, no dispersion formed, very large polymer pieces |
| 2 | 98.48 | 90.700 | 100:28 | acceptable, dispersion formed upon long term shear, small particles |
| 3 | 98.39 | 20.200 | 100:44 | moderate, dispersion formed after short term shear, small particles |
| 4 | 97.45 | 1.000 | 100:56 | excellent, instantaneous formation of a fine long term stable dispersion |
| 5 | 98.02 | 12.800 | 100:52 | moderate, dispersion formed after short term shear, small particles |

*4 g of polyorganosiloxane material were added to 200 g of water and subjected to mixing with an Ultra Thurrax at 9500 RPM.
**13C-NMR The data show that example 1 yields a material which contains some ester functions but is too high in viscosity. As a consequence a very poor, uneven, lumpy and sticky dispersion in water is formed. Examples 2 to 4 show that reaction protocols according to the invention yield low viscosity materials which can be dispersed to small particles. The lower the viscosity the faster a dispersion is reached and the more stable the dispersion.

Example 6

Inventive Polyorganosiloxane Composition

The product of example 1 is mixed with a lauroyl ester modified siloxane of the structure

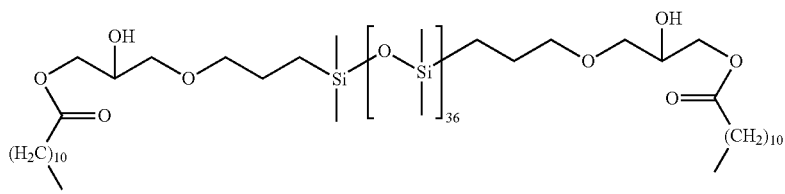

which was synthesized from the corresponding epoxysiloxane, lauric acid and triethylamine (catalyst) in propylene glycol monomethyl ether according to WO 2011/064255.

The blending experiments are summarized in tab.2.

TABLE 2

| Example # | Weight ratio example 1:lauryl ester | Viscosity mPas 20° C., spindle 4, 12 RPM | Dispersibility in water* |
|---|---|---|---|
| 6.1 | 100:0 | 121.000 | very poor, no dispersion formed, very large polymer pieces |
| 6.2 | 90:10 | 77.300 | acceptable, dispersion formed upon long term shear, small particles |
| 6.3 | 75:25 | 32.000 | moderate, dispersion formed after short term shear, small particles |
| 6.4 | 50:50 | 4.200 | moderate, dispersion formed after short term shear, small particles |
| 6.5 | 25:75 | 500 | good, instantaneous formation of a long term stable dispersion |
| 6.6 | 0:100 | 106** | poor, instantaneous formation of a dispersion, rapid separation |

*4 g of the polyorganosiloxane blends were added to 200 g of water and subjected to mixing with an Ultra Thurrax at 9500 RPM.
**measured at 60 RPM The data for the examples 6.2 to 6.5 in tab.2 show that the physical blending of the non-inventive material of example 1 with an ester modified siloxane yields mixtures which can be dispersed in water.

The invention claimed is:

1. A polyorganosiloxane compound comprising:
   at least one polyorganosiloxane group (a),
   at least one quaternary ammonium group (b),
   at least one terminal ester group (c),
   at least one functional organic group (d), comprising one or more hydroxyl groups and at least one functional group selected from an ester group, an ether group and an amino group, and
   wherein the molar ratio of the quaternary ammonium groups (b) and the terminal ester groups (c) is less than 100:15 and
   wherein the polyorganosiloxane compound comprises at least one unit of the formula (I):

$$[-CH_2-X-CH_2-D-] \qquad (I)$$

wherein
D is selected from the group consisting of:

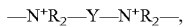

a saturated or unsaturated mono or diquaternary heterocycle of the formulae

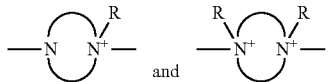

and an aromatic ammonium heterocycle of the formula

wherein
X is at least one group $X^1$ and at least one group $X^2$, wherein
$X^1$ is a difunctional organic group, comprising three or more hydroxyl groups and at least one functional group selected from the group consisting of an ester group, an ether group and an amino group, and wherein said group $X^1$ does not comprise a polydiorganosiloxane group,
$X^2$ is a difunctional organic group, comprising at least one polydiorganosiloxane group,
R can be the same or different is selected from monovalent organic groups having up to 22 carbon atoms and optionally one or more heteroatoms, and
Y is a difunctional organic group optionally comprising one or more heteroatoms.

2. A polyorganosiloxane compound according to claim 1, wherein the terminal ester group (c) is selected from the group consisting of carboxylic acid ester groups, sulfonic acid ester groups, sulfuric acid ester groups, and phosphoric acid mono- or diester groups.

3. A polyorganosiloxane compound according to claim 1, wherein the units of the formula (I) are selected from formula (Ia):

[—CH$_2$—X—CH$_2$—N$^+$R$_2$—Y—N$^+$R$_2$—]    (Ia)

wherein X, R and Y are as defined.

4. A polyorganosiloxane compound according to claim 3, wherein the units of the formula (Ia) are selected from the group consisting of:

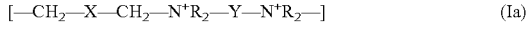

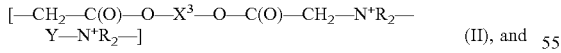

wherein R and Y are as defined above,
$X^3$ is both $X^{31}$ and $X^{32}$,
wherein
$X^{31}$ is selected from a difunctional organic group, comprising three or more hydroxyl groups and at least one functional group selected from the group consisting of an ester group, an ether group and an amino group, and wherein said group $X^{31}$ does not comprise a polydiorganosiloxane group, $X^{32}$ is a difunctional organic group, comprising at least one polydiorganosiloxane group,
and
$X^4$ is both $X^{41}$ and $X^{42}$,
wherein
$X^{41}$ is selected from a difunctional organic group, comprising three or more hydroxyl groups and at least one functional group selected from the group consisting of an ester group, an ether group and an amino group, and wherein said group $X^{41}$ does not comprise a polydiorganosiloxane group,
$X^{42}$ is a difunctional organic group, comprising at least one polydiorganosiloxane group.

5. A polyorganosiloxane compound according to claim 4, comprising units of the formula (II) and of the formula (III).

6. A polyorganosiloxane compound according to claim 4, wherein
$X^{41}$ is selected from the group consisting of
a group of formula (IV):

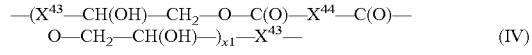

wherein $X^{43}$ is a difunctional organic group, comprising three or more hydroxyl groups and at least one functional group selected from the group consisting of an ester group, an ether group and an amino group, $X^{44}$ is an optionally substituted difunctional organic group, optionally comprising one or more heteroatoms, and x1 is ≥1,
and a group of formula (V):

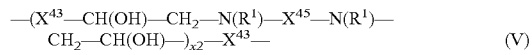

wherein $X^{43}$ is as defined above, $X^{45}$ is a difunctional organic group, optionally comprising one or more heteroatoms, $R^1$ is selected from the group consisting of hydrogen and a C1-C6 alkyl group, and x2 is ≥1,
$X^{31}$ is selected from the group consisting of
a group of formula (VI):

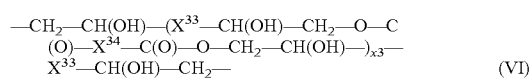

wherein $X^{33}$ is a difunctional organic group, comprising three or more hydroxyl groups and at least one functional group selected from the group consisting of an ester group, an ether group and an amino group, $X^{34}$ is a difunctional organic group, optionally comprising one or more heteroatoms, and x3 is ≥1,
and a group of formula (VII):

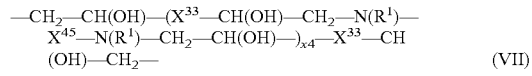

wherein $X^{33}$, $X^{45}$ and $R^1$ are as defined above, and x4 is ≥1.

7. A polyorganosiloxane compound according to claim 1, wherein formula (I) is selected from the group consisting of:

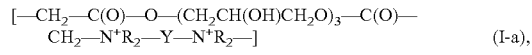

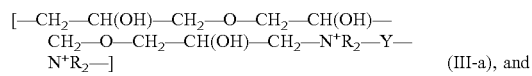

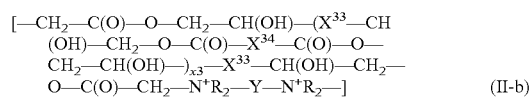

wherein $X^{33}$ is a moiety of the following formula:

—CH₂—O—CH₂—CH(OH)—CH₂—O—CH₂— and wherein $X^{34}$ is a moiety of the following formula:

—CH(OH)—CH(OH)— and wherein R and Y are each as defined and $x3 \geq 1$.

8. A polyorganosiloxane compound according to claim 1, comprising more than one unit of the formula (I).

9. A polyorganosiloxane compound according to claim 1, wherein the group $X^1$ is of the formula (VIII):

-A-E-A'-    (VIII)

wherein A and A' each are independently selected from the group consisting of a single bond and a divalent organic group having up to 10 carbon atoms and optionally one or more hetero atoms, and E is selected from the group consisting of the formulas

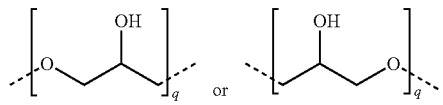

wherein q is independently from each other $\geq 1$, ------ and denotes a single bond,

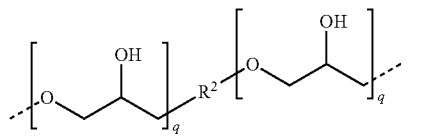

wherein ------ denotes a single bond, $R^2$ is an optionally substituted, divalent straight chain, cyclic aliphatic and/or branched and/or aromatic hydrocarbon residue with up to 40 carbon atoms, which optionally contains one or more heteroatoms selected from O or N, and wherein each q is independently $\geq 1$, and

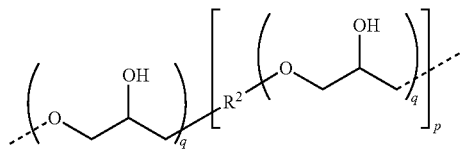

wherein ------ denotes a single bond, $R^2$ is as defined above, each q independently is $\geq 1$, and p is $>1$, with the proviso that A and E or A' and E are not bonded via two hetero atoms and provided that E contains three or more hydroxy groups.

10. A polyorganosiloxane compound according to claim 1, wherein group $X^1$ is of the formula (VIII) -A-E-A¹ (VIII) wherein A and A' each are independently selected from the group consisting of a single bond and a divalent organic group having up to 10 carbon atoms and optionally one or more hetero atoms, and E is a group $E^4$ of formula:

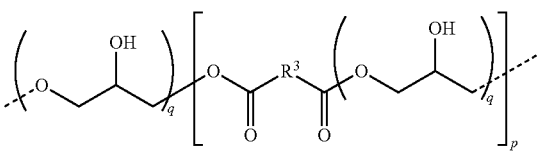

wherein ------ denotes a single bond, $R^3$ is an optionally substituted, bivalent straight chain, cyclic aliphatic and/or branched and/or aromatic hydrocarbon residue with up to 38 carbon atoms, optionally containing one or more heteroatoms selected from the group consisting of O and N, and each q is $\geq 1$, and may be the same or different, p is $\geq 1$, with the proviso that A and E or A' and E are not bonded via two hetero atoms, and provided that E contains three or more hydroxy groups.

11. A polyorganosiloxane compound according to claim 1, wherein the functional organic group d) has the formula (VIII), -A-E-A¹ (VIII), wherein A and A' each are independently selected from the group consisting of a single bond and a divalent organic group having up to 10 carbon atoms and optionally one or more hetero atoms, wherein E is selected from the groups of the following general formulae $E^5$, $E^6$ and $E^7$:

-{[GLY'-GLY''-GLY']-ACD}$_{q1}$-GLY'$_{q2}$-,    $E^5$:

-{[GLY'-GLY''-GLY''']-AM}$_{q1}$-GLY'$_{q2}$-, and    $E^6$:

-{[GLY'-GLY''-GLY''']-AM}$_{q1}$-GLY'''$_{q2}$-,    $E^7$:

with
q1=0 to 12,
q2>0
q1+q2=1 to 24,
GLY'=—CH₂CH(OH)CH₂O—
GLY''=—R₄—O—
GLY'''=—CH₂CH(OH)CH₂—
ACD=—C(O)—R⁵—C(O)O—
AM=—N(R₆)—R⁵—N(R₆)—

$R^6$ is selected from C1-C22-alkyl, C1-C22-fluoroalkyl or aryl or part of a ring system with $R^5$, $R^5$ is selected from a bivalent straight chain, cyclic and/or branched C2-C40 hydrocarbon residue which is optionally interrupted by —O—, trivalent N, —NR⁶—, —C(O)—, —C(S)—, and optionally substituted with —OH, or part of a ring system with $R^6$, wherein $R^6$ is defined as above, $R^4$ is selected from a divalent straight chain, cyclic and/or branched and/or aromatic C2-C40 hydrocarbon residue which is optionally interrupted by —O—, —C(O)—, —C(S)—, and optionally substituted with —OH, and provided that E contains three or more hydroxy groups.

12. Polyorganosiloxane compounds according to claim 1, wherein the at least one polyorganosiloxane group (a) comprises a divalent group of the general formula (IX):

—K—S—K—    (IX)

where
S is a siloxane moiety of the formula (X):

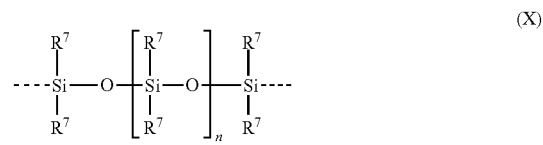

wherein ------ denotes a single bond to K,
wherein $R^7$ is selected from C1-C22-alkyl, C1-C22-fluoralkyl or aryl,
n is 0 to 1000,
K is selected from a bivalent or trivalent straight chain, cyclic and/or branched C2-C40 hydrocarbon residue which is optionally interrupted by —O—, —NH—, trivalent N, —$NR^7$—, —C(O)—, —C(S)—, and optionally substituted with —OH, wherein $R^7$ is as defined, and whereby the residues K can be identical or different from each other.

13. Polyorganosiloxane compounds according to claim 1, wherein $X^2$ has the formula (IX):

—K—S—K— (IX)

where
S is a siloxane moiety of the formula (X):

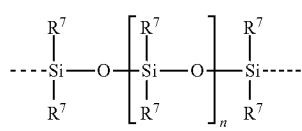    (X)

wherein ------ denotes a single bond to K,
wherein $R^7$ is selected from C1-C22-alkyl, C1-C22-fluoralkyl or aryl,
n is 0 to 1000,
K is selected from a bivalent or trivalent straight chain, cyclic and/or branched C2-C40 hydrocarbon residue which is optionally interrupted by —O—, —NH—, trivalent N, —$NR^7$—, —C(O)—, —C(S)—, and optionally substituted with —OH, wherein $R^7$ is as defined and whereby the residues K can be identical or different from each other.

14. A polyorganosiloxane compound according to claim 9, wherein A and A' are independently selected from the group consisting of:
a single bond,
—C(O)—
O—C(O)—
C(O)—O—
$CH_2$—C(O)—O—
O—C(O)—$CH_2$—
$CH_2CH_2$—C(O)—O—
O—C(O)—$CH_2$—$CH_2$—
$CH_2CH_2CH_2$—C(O)—O—
O—C(O)—$CH_2$—$CH_2$—$CH_2$—
$CH_2CH_2$—O—
O—$CH_2CH_2$—
C(O)—$CH_2$—
$CH_2$—C(O)—
C(O)—$CH_2CH_2$—
$CH_2CH_2$—C(O)—
C(O)—$CH_2CH_2CH_2$—
$CH_2CH_2CH_2$—C(O)—
—$CH_2CH_2$—,
$N(R^6)$—$R^5$—$N(R^6)$— with $R^6$ and $R^5$ are defined as $R^6$ is selected from C1-C22-alkyl, C1-C22-fluoroalkyl or aryl or part of a ring system with $R^5$, $R^5$ is selected from a bivalent straight chain, cyclic and/or branched C2-C40 hydrocarbon residue which is optionally interrupted by —O—, trivalent N, —$NR^6$—, —C(O)—, —C(S)—, and optionally substituted with —OH, or part of a ring system with $R^6$, CH(OH)—$CH_2$—,
O—$CH_2$—CH(OH)—,
—CH(OH)—$CH_2$—O—, and
$CH_2$—CH(OH)—.

15. A polyorganosiloxane compound according to claim 1, wherein the terminal ester groups (c) are selected from the group consisting of:
—OC(O)—Z,
—$OS(O)_2$—Z,
$OS(O_2)O$—Z,
—OP(O)(O—Z)OH, and
—$OP(O)(O—Z)_2$
wherein Z is selected from monovalent organic residues having up to 40 carbon atoms, optionally comprising one or more hetero atoms.

16. A polyorganosiloxane compound according to claim 1 of the general formulas (Ib) and (Ic):

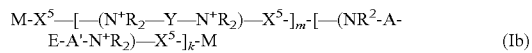  (Ib)

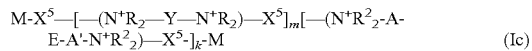  (Ic)

wherein:
m is >0, k is an average value of >0 to 50, M represents a terminal group, comprising terminal ester groups selected from
—OC(O)—Z,
$OS(O)_2$—Z,
—$OS(O_2)O$—Z,
—OP(O)(O—Z)OH, and
—$OP(O)(O—Z)_2$
wherein Z is a monovalent organic residue having up to 40 carbon atoms and optionally one or more heteroatoms
A and A' each are independently selected from the group consisting of a single bond and a divalent organic group having up to 10 carbon atoms and optionally one or more hetero atoms,
E is selected from the group of the formulas

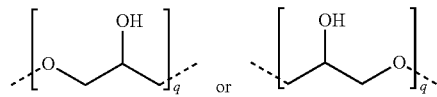

wherein q is independently from each other ≥1, preferably q is 3, and ------ denotes a single bond,

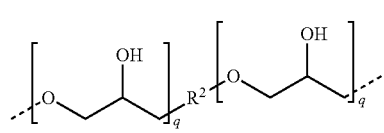

wherein ------ denotes a single bond, $R^2$ is an optionally substituted, divalent straight chain, cyclic aliphatic and/or branched and/or aromatic hydrocarbon residue with up to 40 carbon atoms, which optionally contains one or more heteroatoms selected from O or N, and wherein each q is independently ≥1, and

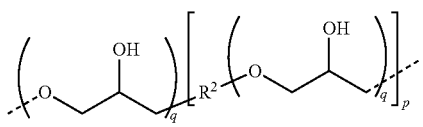

wherein ------ denotes a single bond, $R^2$ is as defined above, each q independently is ≥1, and p is >1, with the proviso that A and E or A' and E are not bonded via two hetero atoms, provided that E contains three or more hydroxy groups, R is selected from monovalent organic groups having up to 22 carbon atoms, and optionally one or more heteroatoms, $R^2$ is an optionally substituted, bivalent straight chain, cyclic aliphatic and/or branched and/or aromatic hydrocarbon residue with up to 40 carbon atoms, which may contain one or more heteroatoms selected from O and N, $X^5$ is a group of the formula:
—K—S—K— where S is a siloxane moiety of the formula (X):

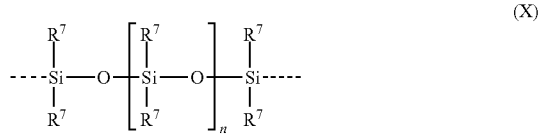

wherein ------ denotes a single bond to K, wherein $R^7$ is selected from C1-C22-alkyl, C1-C22-fluoralkyl or aryl, n is 0 to 1000, K is selected from a bivalent or trivalent straight chain, cyclic and/or branched C2-C40 hydrocarbon residue which is optionally interrupted by —O—, —NH—, trivalent N, —$NR^7$—, —C(O)—, —C(S)—, and optionally substituted with —OH, wherein $R^7$ is as defined as above, and whereby the residues K can be identical or different from each other, and Y is a difunctional organic group containing one or more heteroatoms.

17. A process for the manufacture of the polyorganosiloxane compounds according to claim 1, which comprises the reaction of:
(i) at least one ditertiary diamine,
(ii) at least one amino-alkylating compound,
(iii) at least one monofunctional organic acid,
(iv) at least one difunctional compound comprising three or more hydroxyl groups and at least one functional group selected from the group consisting of an ester group, an ether group and an amino group, and
wherein at least one compound among compounds (i) and (ii) comprises a polyorganosiloxane structural unit.

18. A polyorganosiloxane compound as prepared by the process of claim 17.

19. A polyorganosiloxane composition, comprising:
A) a polyorganosiloxane compound comprising:
at least one polyorganosiloxane group (a),
at least one quaternary ammonium group (b),
at least one terminal ester group (c),
at least one functional organic group (d), comprising one or more hydroxyl groups and at least one functional group selected from the group consisting of an ester group, an ether group and an amino group, and
wherein the polyorganosiloxane compound comprises at least one unit of the formula (I):

[—CH$_2$—X—CH$_2$-D-]    (I)

wherein
D is selected from the group consisting of:

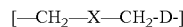

a saturated or unsaturated mono or diquaternary heterocycle of the formulae

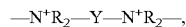

and an aromatic ammonium heterocycle of the formula

wherein
X is at least one group $X^1$ and at least one group $X^2$, wherein
$X^1$ is a difunctional organic group, comprising three or more hydroxyl groups and at least one functional group selected from the group consisting of an ester group, an ether group and an amino group, and wherein said group $X^1$ does not comprise a polydiorganosiloxane group
$X^2$ is a difunctional organic group, comprising at least one polydiorganosiloxane group,
R can be the same or different is selected from monovalent organic groups having up to 22 carbon atoms and optionally one or more heteroatoms, and
Y is a difunctional organic group optionally comprising one or more heteroatoms and B) at least one polyorganosiloxane compound, comprising at least one terminal ester group, which polyorganosiloxane compound is different from polyorganosiloxane compound A).

20. Aqueous emulsions comprising at least one polyorganosiloxane compound as defined in claim 1.

21. Aqueous emulsions comprising at least one polyorganosiloxane composition as defined in claim 19.

22. Cosmetic compositions or formulations, comprising at least one polyorganosiloxane compound as defined in claim 1.

23. Cosmetic compositions or formulations, comprising at least one polyorganosiloxane composition as defined in claim 19.

24. Cosmetic compositions or formulations according to claim 22, selected from the group consisting of skin care compositions, hair care compositions, selected from conditioners, including rinse off and leave on conditioners, shampoos, including anionic shampoo, cationic shampoo, non-ionic shampoo and amphoteric shampoo, hair setting formulations, clear rinse-off hair setting agents, hair foam setting formulations, hair mousses, hair styling gels, hair styling sprays, hair dyes, hair color products, and pump sprays, hair bleaches, waving products, hair straighteners, deodorants, antiperspirants, antiperspirant/deodorants, shaving products, skin lotions, moisturizers, toners, bath products, cleansing products, manicure products, protective creams, and color cosmetics.

25. Cosmetic compositions or formulations according to claim 23, selected from the group consisting of skin care compositions, hair care compositions, selected from conditioners, including rinse off and leave on conditioners, shampoos, including anionic shampoo, cationic shampoo, nonionic shampoo and amphoteric shampoo, hair setting formulations, clear rinse-off hair setting agents, hair foam setting formulations, hair mousses, hair styling gels, hair styling sprays, hair dyes, hair color products, and pump sprays, hair bleaches, waving products, hair straighteners, deodorants, antiperspirants, antiperspirant/deodorants, shaving products, skin lotions, moisturizers, toners, bath products, cleansing products, manicure products, protective creams, and color cosmetics.

26. The polyorganosiloxane compound of claim 1 wherein the compound is a linear copolymer compound wherein the functional groups (a)-(d) are present in at least two repeating units.

27. The polyorganosiloxane compound of claim 26 wherein the at least one terminal ester group (c) is a result of the use of monofunctional organic acids as chain stoppers.

\* \* \* \* \*

UNITED STATES PATENT AND TRADEMARK OFFICE
CERTIFICATE OF CORRECTION

| | | |
|---|---|---|
| PATENT NO. | : 10,160,834 B2 | Page 1 of 1 |
| APPLICATION NO. | : 15/209121 | |
| DATED | : December 25, 2018 | |
| INVENTOR(S) | : Wagner et al. | |

It is certified that error appears in the above-identified patent and that said Letters Patent is hereby corrected as shown below:

On the Title Page

Item (73), the assignee information was incorrectly recited as:
Momentive Performance Materials Inc. Waterford, New York, And should instead have been recited as:
Momentive Performance Materials GMBH Leverkusen, Germany Signed and Sealed this
Twenty-fourth Day of September, 2019

Andrei Iancu
*Director of the United States Patent and Trademark Office*